(12) United States Patent
Reichard et al.

(10) Patent No.: US 6,204,265 B1
(45) Date of Patent: Mar. 20, 2001

(54) SUBSTITUTED OXIMES AND HYDRAZONES AS NEUROKININ ANTAGONISTS

(75) Inventors: Gregory A. Reichard, Morris Plains; Neng-Yang Shih, North Caldwell; Dasong Wang, Union, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/468,591

(22) Filed: Dec. 21, 1999

Related U.S. Application Data

(60) Provisional application No. 60/113,404, filed on Dec. 23, 1998.

(51) Int. Cl.$^7$ .................. C07D 239/04; C07D 413/04; C07D 401/04; A61K 31/4468; A61K 31/496
(52) U.S. Cl. .................. 514/235.8; 546/210; 514/326; 514/274; 544/123; 544/316; 544/318
(58) Field of Search .................. 546/210; 514/326, 514/123, 235.8, 274; 544/316, 318

(56) References Cited

U.S. PATENT DOCUMENTS

| | | | |
|---|---|---|---|
| 5,688,960 | 11/1997 | Shankar | 546/202 |
| 5,696,267 | 12/1997 | Reichard et al. | 546/217 |
| 5,789,422 | 8/1998 | Reichard et al. | 514/327 |
| 5,840,725 | 11/1998 | Reichard et al. | 514/252 |
| 5,945,428 | 8/1999 | Shih et al. | 514/278 |

FOREIGN PATENT DOCUMENTS

| | | |
|---|---|---|
| WO 95/05377 | 2/1995 | (WO) . |
| WO 99/26924 | 6/1999 | (WO) . |

OTHER PUBLICATIONS

Chung et al, *Molecular Pharmacology*, 48 (1995), p. 711–716.
Stratton et al, *Eur. J. Pharmacol.*, 250 (1993), p. R11–R12.
Walsh et al, *Psychopharmacology*, 121 (1995), p. 186–191.
Lecci et al, *Neuroscience Let.*, 129 (1991), p. 299–302.
Teixeira et al, *Eur. J. Pharmacol.*, 311 (1996), p. 7–14.
Picard et al, *Eur. J. Pharmacol.*, 232 (1993), p. 255–261.
Fleetwood–Walker et al, *Eur. J. Pharmacol.*, 242 (1993), p. 173–181.
Kramer, et al, *Science*, 281 (1998), p. 1640–1645.
Gao and Peet, Recent Advances in Neurokinin Receptor Antagonists, Curr. Med. Chem., 6, 375–388, 1999.*

* cited by examiner

*Primary Examiner*—Richard L. Raymond
*Assistant Examiner*—Hong Liu
(74) *Attorney, Agent, or Firm*—Anita W. Magatti

(57) ABSTRACT

Compound represented by the structural formula $$Z-(C)_a-\overset{\overset{A}{\|}}{\underset{\underset{Q}{|}}{C}}-\underset{R^{7a}}{\overset{R^{6a}}{|}}{(C)_d}-X-\underset{R^{8a}}{\overset{R^{9a}}{|}}{(C)_b}-T \qquad I$$

or a pharmaceutically acceptable salt thereof, wherein:
a is 0–3;
b, d and e are 0–2;
R is H, alkyl, F or —OR$^6$;
A is an optionally substituted oxime or hydrazone;
d is not 0 and X is a bond, —C(O)—, —O—, —NR$^9$—, —S(O)$_e$—, —N(R$^6$)C(O)—, —C(O)N(R$^6$)—, —OC(O)NR$^6$—, —OC(=S)NR$^6$—, —N(R$^6$)C(=S)O—, —S(O)$_2$N(R$^6$)—, —N(R$^6$)S(O)$_2$—, —N(R$^6$)C(O)O—, —OC(O)— or —N(R$^6$)C(O)NR$^7$—; or d is 0 and X is a bond or —NR$^6$—;
T is H, aryl, heterocycloalkyl or heteroaryl;
Q is phenyl, naphthyl or heteroaryl;
R$^6$ is H, alkyl, hydroxyalkyl, alkoxyalkyl, phenyl, and benzyl;
R$^9$ is R$^6$ or —OR$^6$
R$^{6a}$, R$^{7a}$, R$^{8a}$ and R$^{9a}$ are H or alkyl;
Z is a nitrogen-containing heterocyclo group, e.g., piperidinyl, substituted by a heterocyclo- or heterocycloalkyl group;
wherein phenyl, benzyl, aryl, heterocycloalkyl, heteroaryl and cycloalkyl groups are optionally substituted; methods of treating diseases such as asthma, cough, bronchospasm, depression, emesis, imflammatory diseases, and gastrointestinal disorders with said compounds, and pharmaceutical compositions comprising said compounds are disclosed.

13 Claims, No Drawings

SUBSTITUTED OXIMES AND HYDRAZONES AS NEUROKININ ANTAGONISTS

CROSS REFERENCE TO RELATED APPLICATIONS

This application claims the benefit of U.S. Provisional Application No. 60/113,404, filed Dec. 23, 1998.

BACKGROUND OF THE INVENTION

The present invention relates to a genus of substituted oximes and hydrazones useful as antagonists of tachykinin receptors, in particular as antagonists of the neuropeptides neurokinin-1 receptor ($NK_1$) and/or neurokinin-2 receptor ($NK_2$) and/or neurokinin-3 receptor ($NK_3$).

Neurokinin receptors are found in the nervous system and the circulatory system and peripheral tissues of mammals, and therefore are involved in a variety of biological processes. Neurokinin receptor antagonists are consequently expected to be useful in the treatment or prevention of various mammalian disease states, for example asthma, cough, bronchospasm, inflammatory diseases such as arthritis, central nervous system conditions such as migraine and epilepsy, nociception, depression, and various gastrointestinal disorders such as Crohn's disease.

In particular, $NK_1$ receptors have been reported to be involved in microvascular leakage and mucus secretion, and $NK_2$ receptors have been associated with smooth muscle contraction, making $NK_1$ and $NK_2$ receptor antagonists especially useful in the treatment and prevention of asthma.

Substituted oxime and hydrazone $NK_1$ and $NK_2$ receptor antagonists have previously been disclosed in U.S. Pat. Nos. 5,696,267, 5,688,960, and 5,789,422.

SUMMARY OF THE INVENTION

Compounds of the present invention are represented by the formula I

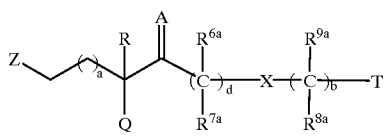

I or a pharmaceutically acceptable salt thereof, wherein:

a is 0, 1, 2 or 3;

b and d are independently 0, 1 or 2;

R is H, $C_{1-6}$ alkyl, —$OR^6$ or —F;

A is =N—$OR^1$ or =N—N($R^2$)($R^3$);

when d is not 0, X is a bond, —C(O)—, —O—, —$NR^9$—, —S(O)$_e$—, —N($R^6$)C(O)—, —C(O)N($R^6$)—, —OC(O)N$R^6$—, —OC(=S)N$R^6$—, —N($R^6$)C(=S)O—, —S(O)$_2$N($R^6$)—, —N($R^6$)S(O)$_2$—, —N($R^6$)C(O)O—, —OC(O)— or —N($R^6$)C(O)N$R^7$; and when d is 0, X is a bond or —N$R^6$—;

T is H, $R^4$-aryl, $R^4$-heterocycloalkyl or $R^4$-heteroaryl;

Q is $R^5$-phenyl, $R^5$-naphthyl or $R^5$-heteroaryl;

$R^1$ is H, $C_{1-6}$ alkyl, —(C($R^6$)($R^7$))$_n$—G, —$G^2$, —(C($R^6$)($R^7$))$_p$—M—(C($R^{13}$)($R^{14}$))$_n$—G or —(C($R^6$)($R^7$))$_p$—M—($R^4$-heteroaryl);

$R^2$ and $R^3$ are independently selected from the group consisting of H, $C_{1-6}$ alkyl, —(C($R^6$)($R^7$))$_n$—G, —$G^2$ and —S(O)$_e R^{13}$; or $R^2$ and $R^3$, together with the nitrogen to which they are attached, form a ring of 5 to 6 members, wherein 0, 1 or 2 ring members are selected from the group consisting of —O—, —S— and —N($R^{19}$)—;

$R^4$ and $R^5$ are independently 1–3 substituents independently selected from the group consisting of H, halogeno, —$OR^6$, —OC(O)$R^6$, —OC(O)N($R^6$)($R^7$), —N($R^6$)($R^7$), $C_{1-6}$ alkyl, —$CF_3$, —$C_2F_5$, —$COR^6$, —$CO_2R^6$, —CON($R^6$)($R^7$), —S(O)$_e R^{13}$, —CN, —$OCF_3$, —$OCHF_2$, —$NR^6CO_2R^{16}$, —$NR^6COR^7$, —$NR^8CON(R^6)(R^7)$, $NO_2$, —N($R^6$)S(O)$_2 R^{13}$ or —S(O)$_2$N($R^6$)($R^7$); or adjacent $R^4$ substituents or adjacent $R^5$ substituents can form a —O—$CH_2$—O— group;

$R^6$, $R^7$, $R^8$, $R^{13}$ and $R^{14}$ are independently selected from the group consisting of H, $C_{1-6}$ alkyl, $C_2$–$C_6$ hydroxyalkyl, $C_1$–$C_6$ alkoxy-$C_1$–$C_6$ alkyl, $R^{15}$-phenyl, and $R^{15}$-benzyl;

$R^9$ is independently selected from the group consisting of $R^6$ and —$OR^6$;

or $R^6$ and $R^7$, or $R^7$ and $R^9$, together with the nitrogen to which they are attached, form a ring of 5 to 6 members, wherein 0, 1 or 2 ring members are selected from the group consisting of —O—, —S— and —N($R^{19}$)—;

$R^{6a}$, $R^{7a}$, $R^{8a}$, $R^{9a}$, $R^{10}$ and $R^{10a}$ are independently selected from the group consisting of H and $C_{1-6}$ alkyl;

$R^{15}$ is 1 to 3 substituents independently selected from the group consisting of H, —OH, $C_1$–$C_6$ alkyl, $C_1$–$C_6$ alkoxy, $C_1$–$C_6$ alkylthio, halogeno, —$CF_3$, —$C_2F_5$, —$COR^{10}$, —$CO_2R^{10}$, —C(O)N($R^{10}$)$_2$, —S(O)$_e R^{10a}$, —CN, —N($R^{10}$)$COR^{10}$, —N($R^{10}$)CON($R^{10}$)$_2$ and —$NO_2$;

$R^{16}$ is $C_{1-6}$ alkyl, $R^{15}$-phenyl or $R^{15}$-benzyl;

$R^{19}$ is H, $C_1$–$C_6$ alkyl, —C(O)N($R^{10}$)$_2$ or —$CO_2R^{10}$;

n and p are independently 1–6;

G is selected from the group consisting of H, $R^4$-aryl, $R^4$-heterocycloalkyl, $R^4$-heteroaryl, $R^4$-cycloalkyl, —$CH_2F$, —$CHF_2$, —$CF_3$, —$OR^6$, —N($R^6$)($R^7$), —$COR^6$, —$CO_2R^6$, —CON($R^7$)($R^9$), —S(O)$_e R^{13}$, —$NR^6CO_2R^{16}$, —$NR^6COR^7$, —$NR^8CON(R^6)(R^7)$, —N($R^6$)S(O)$_2 R^{13}$, —N($R^6$)S(O)$_2$N($R^{33}$)($R^{34}$), —S(O)$_2$ N($R^6$)($R^7$), —OC(O)$R^6$, —OC(O)N($R^6$)($R^7$), —C(=N$R^8$)N($R^6$)($R^7$), —C(=N$R^{25}$)N($R^6$)($R^7$), —N($R^8$)C(=N$R^{25}$)N($R^6$)($R^7$), —CN, —C(O)N($R^6$)OR$^7$, and —C(O)N($R^9$)-($R^4$-heteroaryl), provided that when n is 1, G is not —OH or —N($R^6$)($R^7$);

M is selected from the group consisting of a double bond, —O—, —N($R^6$)—, —C(O)—, —C($R^6$)(O$R^7$)—, —C($R^8$) (N($R^6$)($R^7$))—, —C(=N$OR^6$)N($R^7$)—, —C(N($R^6$)($R^7$))=NO—, —C(=N$R^{25}$)N($R^6$)—, —C(O)N($R^9$)—, —N($R^9$) C(O)—, —C(=S)N($R^9$)—, —N($R^9$)C(=S)— and —N($R^6$) C(O)N($R^7$)—, provided that when n is 1, G is not OH or —NH($R^6$); and when p is 2–6, M can also be —N($R^6$)C (=N$R^{25}$)N($R^7$)— or —OC(O)N($R^6$)—;

$G^2$ is $R^4$-aryl, $R^4$-heterocycloalkyl, $R^4$-heteroaryl, $R^4$-cycloalkyl, —$COR^6$, —$CO_2R^{16}$, —S(O)$_2$N($R^6$) ($R^7$) or —CON($R^6$)($R^7$);

e is 0, 1 or 2, provided that when e is 1 or 2, $R^{13}$ and $R^{10a}$ are not H;

$R^{25}$ is H, $C_1$–$C_6$ alkyl, —CN, $R^{15}$-phenyl or $R^{15}$-benzyl;

Z is

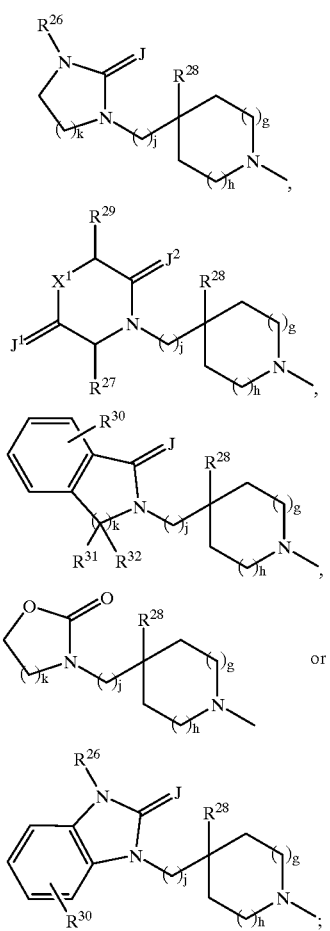

g, h and j are independently 0–2;
k is 1–4;
$X^1$ is —O—, —S— or —$NR^9$—;
J is =O, =S, =$NR^9$, =NCN or =$NOR^1$;
$J^1$ and $J^2$ are independently selected from the group consisting of two hydrogen atoms, =O, =S, =$NR^9$ and =$NOR^1$;
$R^{26}$, $R^{27}$ and $R^{29}$ are independently selected from the group consisting of H, $C_{1-6}$ alkyl, —$(C(R^6)(R^7))_n$—G, —$G^2$, —C(O)—$(C(R^8)(R^9))_n$—G and —$S(O)_e$$R^{13}$;
$R^{28}$ is H, —$(C(R^6)(R^7))_t$—G or —$CON(R^6)(R^7)$;
t is 0, 1, 2 or 3, provided that when j is 0, t is 1, 2 or 3;
$R^{30}$ is 1–3 substituents independently selected from the group consisting of H, halogeno, —$OR^6$, —OC(O)$R^6$, —$OC(O)N(R^6)(R^7)$, —$N(R^6)(R^7)$, $C_{1-6}$ alkyl, —$CF_3$, —$C_2F_5$, —$COR^6$, —$CO_2R^6$, —$CON(R^6)(R^7)$, —$S(O)_eR^{13}$, —CN, —$OCF_3$, —$NR^6CO_2R^{16}$, —$NR^6COR^7$, —$NR^8CON(R^6)(R^7)$, $NO_2$, —$N(R^6)S(O)_2R^{13}$ or —$S(O)_2N(R^6)(R^7)$; or adjacent $R^{30}$ substituents can form a —O—$CH_2$—O— group;
$R^{31}$ is independently selected from the group consisting of H and $C_1$-$C_6$ alkyl;
$R^{32}$ is independently selected from the group consisting of H, —OH and $C_1$-$C_6$ alkoxy; and
$R^{33}$ and $R^{34}$ are independently selected from the group consisting of H, $C_1$-$C_6$ alkyl, $R^{15}$-phenyl and $R^{15}$-benzyl.

Preferred are compounds of formula I wherein X is —O—, —C(O)—, a bond, —$NR^6$—, —$S(O)_e$—, —$N(R^6)C(O)$—, —$OC(O)NR^6$ or —$C(=NOR^1)$—. More preferred are compounds of formula I wherein X is —O—, —$NR^6$—, —$N(R^6)C(O)$— or —$OC(O)NR^6$ Additional preferred definitions are: b is 1 or 2 when X is —O— or —$N(R^6)$—; b is 0 when X is —$N(R^6)C(O)$—; and d is 1 or 2. T is preferably $R^4$-aryl, with $R^4$-phenyl being more preferred. Also preferred are compounds wherein $R^{6a}$, $R^{7a}$, $R^{8a}$ and $R^{9a}$ are independently hydrogen, hydroxyalkyl or alkoxyalkyl, with hydrogen being more preferred. Especially preferred are compounds wherein $R^{8a}$ and $R^{9a}$ are each hydrogen, d and b are each 1, X is —O—, —$NR^6$—, —$N(R^6)C(O)$— or —$OC(O)NR^6$, T is $R^4$-aryl and $R^4$ is two substituents selected from $C_1$-$C_6$ alkyl, halogeno, —$CF_3$ and $C_1$-$C_6$ alkoxy.

Also preferred are compounds of formula I wherein R is hydrogen. Q is preferably $R^5$-phenyl; an especially preferred definition for Q is $R^5$-phenyl, wherein $R^5$ is two halogeno substituents.

Preferred are compounds of formula I wherein A is =N—$OR^1$. $R^1$ is preferably H, alkyl, —$(CH_2)_n$—G, —$(CH_2)_p$—M—$(CH_2)_n$—G or —$C(O)N(R^6)(R^7)$, wherein M is —O— or —$C(O)N(R^9)$— and G is —$CO_2R^6$, —$OR^6$, —$C(O)N(R^7)(R^9)$, —$C(=NOR^8)N(R^9)(R^7)$, —$C(O)N(R^9)$($R^4$-heteroaryl) or $R^4$-heteroaryl. When A is =N—$N(R^2)(R^3)$, $R^2$ and $R^3$ are independently preferably H, $C_1$-$C_6$ alkyl, —$(C(R^6)(R^7))_n$—G or $G^2$.

Preferred definitions of Z are

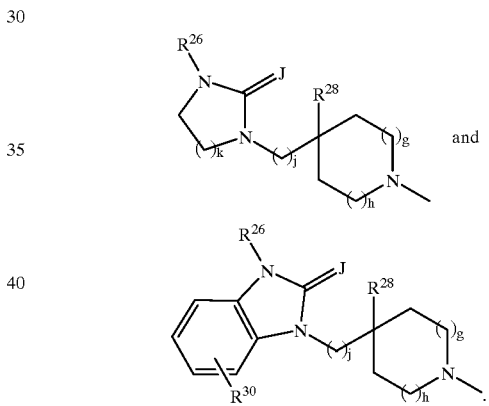

and

Variables g and h are preferably each 1; J is preferably =O; j is preferably 0; k is preferably 1 or 2; and $R^{28}$ is preferably H.

A more defintion of Z is

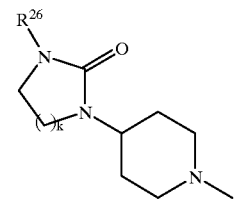

wherein k is preferably 1 or 2.

This invention also relates to the use of a compound of formula I in the treatment of for example respiratory diseases such as chronic lung disease, bronchitis, pneumonia, asthma, allergy, cough, bronchospasm; inflammatory diseases such as arthritis and psoriasis; skin disorders such as atopic dermatitis and contact dermatitis; ophthamalogical disorders such as retinitis, ocular hypertension and cataracts; addictions such as alcohol dependence and stress related disorders; central nervous system conditions such as anxiety, migraine, epilepsy, nociception, emesis, depression, psychosis, schizophrenia, Alzheimer's disease, AIDs related dementia and Towne's disease; gastrointestinal disorders such as Crohn's disease and colitis; bladder disorders; atherosclerosis; fibrosing disorders; and obesity.

In another aspect, the invention relates to a pharmaceutical composition comprising a compound of formula I in a pharmaceutically acceptable carrier. The invention also relates to the use of said pharmaceutical composition in the treatment of the mammalian disease states listed above.

DETAILED DESCRIPTION

As used herein, the term "alkyl" means straight or branched alkyl chains. "Lower alkyl" refers to alkyl chains of 1–6 carbon atoms and, similarly, lower alkoxy refers to alkoxy chains of 1–6 carbon atoms.

"Cycloalkyl" means cyclic alkyl groups having 3 to 6 carbon atoms.

"Aryl" means phenyl, naphthyl, indenyl, tetrahydronaphthyl, indanyl, anthracenyl or fluorenyl.

"Halogeno" refers to fluoro, chloro, bromo or iodo atoms.

"Heterocycloalkyl" refers to 4- to 6-membered saturated rings comprising 1 to 3 heteroatoms independently selected from the group consisting of —O—, —S— and —N($R^{19}$)—, with the remaining ring members being carbon. Examples of heterocycloalkyl rings are tetrahydrofuranyl, pyrrolidinyl, piperidinyl, morpholinyl, thiomorpholinyl and piperazinyl. $R^4$-heterocycloalkyl refers to such groups wherein substitutable ring carbon atoms have an $R^4$ substituent.

"Heteroaryl" refers to 5- to 10-membered single or benzofused aromatic rings comprising 1 to 4 heteroatoms independently selected from the group consisting of —O—, —S— and —N=, provided that the rings do not include adjacent oxygen and/or sulfur atoms. Examples of single-ring heteroaryl groups are pyridyl, isoxazolyl, oxadiazolyl, furanyl, pyrrolyl, thienyl, imidazolyl, pyrazolyl, tetrazolyl, thiazolyl, thiadiazolyl, pyrazinyl, pyrimidinyl, pyridazinyl and triazolyl. Examples of benzofused heteroaryl groups are indolyl, quinolinyl, thianaphthenyl and benzofurazanyl. N-oxides of nitrogen-containing heteroaryl groups are also included. All positional isomers are contemplated, e.g., 1-pyridyl, 2-pyridyl, 3-pyridyl and 4-pyridyl. $R^4$-heteroaryl refers to such groups wherein substitutable ring carbon atoms have an $R^4$ substituent.

Where $R^2$ and $R^3$, or $R^6$ and $R^7$ substituents on a nitrogen atom form a ring and additional heteroatoms are present, the rings do not include adjacent oxygen and/or sulfur atoms or three adjacent hetero-atoms. Typical rings so formed are morpholinyl, piperazinyl and piperidinyl.

In the above definitions, wherein variables $R^6$, $R^7$, $R^8$, $R^{13}$, $R^{14}$, $R^{15}$, $R^{30}$, $R^{31}$ and $R^{32}$, for example, are said to be independently selected from a group of substituents, we mean that $R^6$, $R^7$, $R^8$, $R^{13}$, $R^{14}$, $R^{15}$, $R^{30}$, $R^{31}$ and $R^{32}$ are independently selected, but also that where an $R^6$, $R^7$, $R^8$, $R^{13}$, $R^{14}$, $R^{15}$, $R^{30}$ $R^{31}$ or $R^{32}$ variable occurs more than once in a molecule, those occurrences are independently selected (e.g., if R is —$OR^6$ wherein $R^6$ is hydrogen, X can be —N($R^6$)— wherein $R^6$ is ethyl). Similarly, $R^4$ and $R^5$ can be independently selected from a group of substituents, and where more than one $R^4$ and $R^5$ are present, the substituents are independently selected; those skilled in the art will recognize that the size and nature of the substituent(s) will affect the number of substituents which can be present.

Compounds of formula I can have at least one asymmetrical carbon atom and all isomers, including diastereomers, enantiomers and rotational isomers, as well as E and Z isomers of the oxime, hydrazone and olefin groups, are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of formula I.

Those skilled in the art will appreciate that for some compounds of formula I, one isomer will show greater pharmacological activity than other isomers.

Compounds of the invention have at least one amino group which can form pharmaceutically acceptable salts with organic and inorganic acids. Examples of suitable acids for salt formation are hydrochloric, sulfuric, phosphoric, acetic, citric, oxalic, malonic, salicylic, malic, fumaric, tartaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Compounds of formula I can be prepared using methods well known to those skilled in the art, for example by procedures disclosed in U.S. Pat. No. 5,696,267, incorporated herein by reference. The skilled artisan will recognize that other procedures may be applicable, and that the procedure may be suitably modified to prepare other compounds within the scope of formula I.

Compounds of formula I as defined are preferably prepared as shown in the following reaction scheme as disclosed in U.S. Pat. No. 5,696,267. In the reaction scheme, the variables are as defined above:

Step 1:

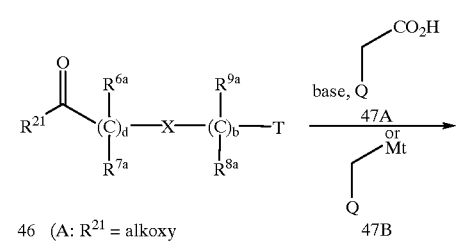

46 (A: $R^{21}$ = alkoxy
B: $R^{21}$ = Cl
C: $R^{21}$ = ——N($CH_3$)O$CH_3$)

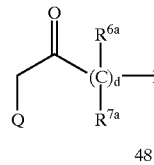

48

In step 1, a compound of formula 47A, wherein Q is as defined above, is reacted with a base such as lithium diisopropylamide (LDA), KHMDS or KH in an inert organic solvent such as THF or DME to generate a dianion. An acid chloride, ester or amide of formula 46A, 46B, or 46C is added to give a ketone of formula 48. Preferable reaction temperatures ranges from −78° C. to 30° C.

Alternatively, compounds of formula 48 can be generated by the reaction of a compound of formula 46, preferably 46C, with a metallated species of formula $QCH_2Mt$ where Mt is a metal, such as lithium or MgHal, wherein "Hal" is halogen. The metallated species $QCH_2Mt$ can be generated by conventional procedures, such as treatment compounds of formula $QCH_2Hal$ with Mg or by treating $QCH_3$ with an organolithium base.

Step 2:

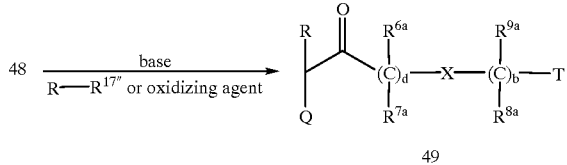

49

In step 2, for compounds wherein R is not hydrogen, the ketone 48 is reacted with a suitable base, such as LDA or KH in an inert organic solvent such as THF. For compounds wherein R is alkyl or hydroxyalkyl, a compound $R—R^{17''}$, wherein $R^{17''}$ is leaving group such as Br, I or triflate is added. For compounds wherein R is OH, an appropriate oxidizing agent such as dimethyldioxirane or Davis reagent is added. Preferable reaction temperatures range from −78° to 50° C. For compounds of the present invention wherein R is H, the ketone 48 is used directly in Step 3.

Step 3:

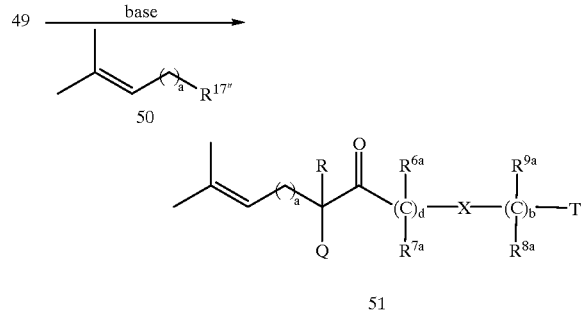

51

In step 3, ketone 49 is reacted with a base such as LDA in a solvent such as THF, then an olefin of formula 50 is added, wherein $R^{17''}$ is as defined above, to give the adduct 51. Preferable reaction temperatures range from −78° C. to 60° C.

Step 4:

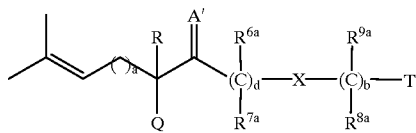

52

In step 4, ketone 51 is reacted with HA', wherein A' is $NH—OR^1$, in an organic solvent such as pyridine or ethanol at a temperature from 25° C. to 150° C. to give a compound of formula 52.

Step 5:

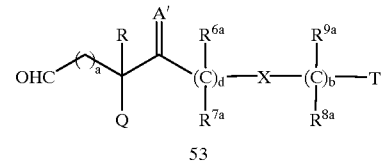

53

In step 5, a compound of formula 52 is oxidized by ozonolysis to give an aldehyde of formula 53. Suitable organic solvents include EtOAc, $CH_3OH$, ethanol, $CH_2Cl_2$ or the like. Preferable reaction temperatures are from −78 to 0° C.

Step 6:

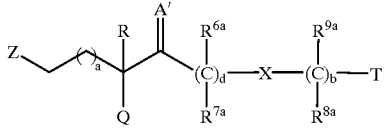

In step 6, an aldehyde of formula 53 is reacted with a compound of formula Z—H, wherein Z is as defined above. The reaction is preferably carried out with a suitably substituted amine (as its acid salt e.g. HCl or maleate or as its free base) and a hydride source such as $NaBH_3CN$ or sodium triacetoxyborohydride in a suitable solvent (e.g. $CH_3OH$, $CH_3CH_2OH$, or $CF_3CH_2OH$ for $NaBH_3CN$, or THF, 1,2-dichloroethane, $CH_3CN$ or $CF_3CH_2OH$ for triacetoxyborohydride), with 3A sieves to obtain the desired product. Any suitable temperature can be used with preferable temperatures between 0° C. and 25° C.

Alternatively, a compound of formula I can be prepared from 51 by the following reaction scheme, wherein the variables are as defined for the cited U.S. patent:

54

Compound 51 is oxidized to a compound of formula 54 under conditions similar to those described for step 5 above. The aldehyde of formula 54 is reacted with a compound of formula Z—H in a manner similar to that described in Step 6, and the resultant ketone is then reacted with a compound of the formula HA' as described above in Step 4 to obtain the compound of formula I.

Starting "ZH" groups are known or are made by procedures known in the art. See, for example, the following Preparations 3–12.

Reactive groups not involved in the above processes can be protected during the reactions with conventional protecting groups which can be removed by standard procedures after the reaction. The following Table 1 shows some typical protecting groups:

TABLE 1

| Group to be Protected | Group to be Protected and Protecting Group |
|---|---|
| —COOH | —COOalkyl, —COObenzyl, —COOphenyl |
| $\diagdown$NH$\diagup$ | $\diagdown$NCOalkyl,$\diagup$  $\diagdown$NCObenzyl,$\diagup$  $\diagdown$NCOphenyl,$\diagup$  $\diagdown$NCH$_2$OCH$_2$CH$_2$Si(CH$_3$)$_3$$\diagup$  $\diagdown$NC(O)OC(CH$_3$)$_3$,$\diagup$  $\diagdown$N-benzyl,$\diagup$  $\diagdown$NSi(CH$_3$)$_3$,$\diagup$  $\diagdown$NSi(CH$_3$)$_2$—C(CH$_3$)$_3$$\diagup$ |
| —NH$_2$ | (succinimide structure) |
| —OH | —OCH$_3$, —OCH$_2$OCH$_3$, —OSi(CH$_3$)$_3$, —OSi(CH$_3$)$_2$—C(CH$_3$)$_3$ or —OCH$_2$phenyl |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation for treatment of asthma, cough, bronchospasm, inflammatory diseases, migraine, nociception, depression, emesis and gastrointestinal disorders may be varied or adjusted from about 1 mg to about 1500 mg, preferably from about 50 mg to about 500 mg, more preferably from about 20 mg to about 200 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 1500 mg/day, in two to four divided doses.

Following are examples of preparing starting materials and compounds of formula I. As used herein, Me is methyl, Bu is butyl, Br is promo, Ac is acetyl, Et is ethyl and Ph is phenyl.

Preparation 1

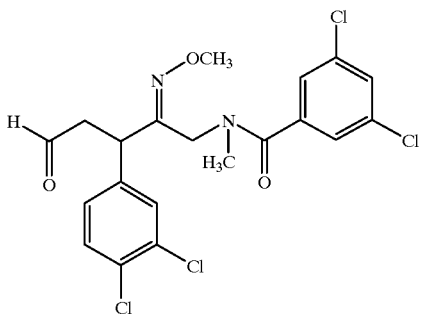

Prepared using methods described in U.S. Pat. No. 5,696,267.

Preparation 2

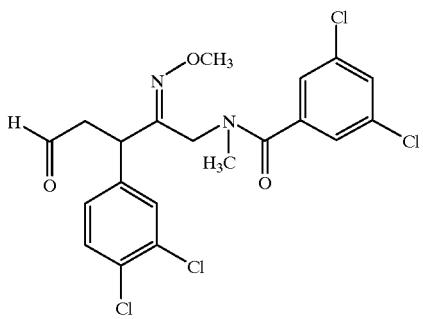

Prepared using methods described in U.S. Pat. No. 5,696,267.

Preparation 3

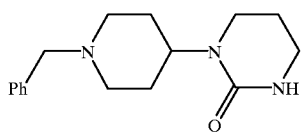

Step 1: Treat a solution of 1-benzyl-4-amino piperidine (25 g, 0.13 mol) in CH$_3$OH (5 mL) with acrylonitrile (9.6 mL, 0.15 mol) at 23° C. Stir for 22 h, and concentrate to yield the crude product.

Step 2: Dissolve the product of Step 1 (31.9 g, 0.13 mol) in CH$_3$OH (1 L) add cobalt (II) chloride (34 g, 0.26 mol) followed by NaBH$_4$ (50 g, 0.13 mol) in several small portion over 45 min at 0° C. Allow the resulting suspension to stir for 1.5 h, carefully acidify with 3 N HCl until the color turns pink. Extract the aqueous solution with ether (Et$_2$O) (1 L), add NaOH at 10° C. until pH=12. Extract the resulting suspension with Et$_2$O (1L), then CH$_2$Cl$_2$ (2×1L). Filter the aqueous layer to remove the solid material, and further extract with CH$_2$Cl$_2$ (3×1L). Concentrate the combined organic layer to give 23.6 g of the desired product.

Step 3: Dissolve the product of Step 2 (10.0 g, 0.41 mol) in anhydrous tetrahydrofuran (THF) (70 mL), treat with carbonyldiimidazole (13.2 g, 0.81 mol), and heat to 60° C. for 14 h. Concentrate the mixture, and filter through a silica plug with CH$_2$Cl$_2$ and CH$_3$OH (sat. with NH$_3$) at a ratio of 94:6 to give 8.6 g of the title product.

Preparation 4

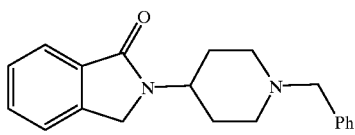

Step 1: Treat a solution of 4-amino-N-benzyl piperidine (20.4 mL, 0.10 mol) in CHCl$_3$ (30 mL) with phthalide anhydride (10.0 g, 0.068 mol) and heat the mixture to reflux at 70° C. for 18 h. Add water and CH$_2$Cl$_2$, separate the layers, extract the aqueous layer with CH$_2$Cl$_2$ (2×40 mL), wash the combined organic layers with brine, concentrate and purify the mixture with column chromatography, eluting with CH$_2$Cl$_2$ and CH$_3$OH (sat. with NH$_3$) at a ratio of 99:1 to give 6.9 g of the desired product.

Step 2: Dissolve the product of Step 1 in acetic acid (HOAc) (10 mL), add zinc dust (1.28 g, 20 mmol) and heat to reflux at 120° C. for 12 h. After cooling the mixture, slowly add NaHCO$_3$ (sat.) solution until pH=10, separate the layers, extract the aqueous layer with CH$_2$Cl$_2$ (2×40 mL), wash the combined organic layers with brine, concentrate the mixture, and purify by column chromatography, eluting with EtOAc:hexane (1:1) with 2% triethylamine (TEA) to give 0.50 g product.

Preparation 5

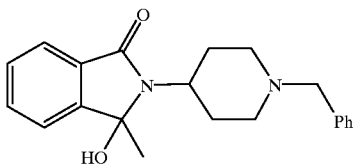

Treat a solution of 4-amino-N-benzyl piperidine (1.0 g, 5.26 mmol) and 2-acetylbenzoic acid (1.0 g, 6.10 mmol) in dichloroethane (10 mL) with NaBH$_3$CN (0.37 g, 6.0 mmol) and stir at 23° C. for 24 h. Heat the mixture to 80° C. for an additional 24 h. Add water (30 mL) and EtOAc (30 mL), filter through celite, separate layers of filtrate and concentrate the organic layer. Purify by column chromatography, eluting with EtOAc:hexane (1:2) with 2% TEA to give 0.86 g product.

Preparation 6

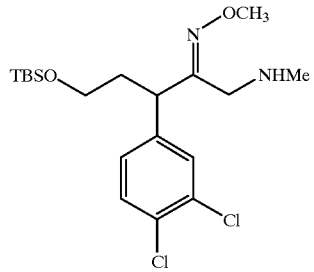

Dissolve the product of Preparation 4, Step 1 (0.76 g, 2.38 mmol) in anhydous THF (6 mL) and add CH$_3$MgBr (3 M, 2 mL, 6 mmol) at 0° C. Warm the mixture and stir at 23° C. for 3 h. Quench with water and CH$_2$Cl$_2$ at 0° C., separate the layers, and extract the aqueous layer with CH$_2$Cl$_2$ (2×40 mL), wash the combined organic layer with brine and concentrate to give 0.68 g product.

Preparation 7

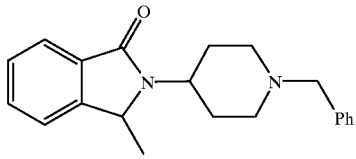

Using procedures known in the art, treat a solution of 3,4-dichlorophenylacetic acid with N-t-BOC-sarcosine methyl ester and separately treat 2-bromo-ethanol with t-butyldimethylsilylchloride. React the product of the first step with NaH, and add the product of the second step and NaI.

Treat the resultant product with 0-methoxyamine HCl, followed by deprotection using HCl in CH$_2$Cl$_2$. Chiral material was obtained by chiral separation using HPLC.

Preparation 8

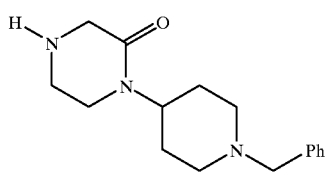

Step 1: Treat a solution of t-butyl-n-(2-aminoethyl) carbamate (18.6 g, 116 mmol) and 1-benzyl-4-piperidone (20 g, 106 mmol) in CH$_2$Cl$_2$ (300 mL) with HOAc (4.1 g, 68 mmol) and sodium triacetoxyborohydride (25 g, 118 mmol) at 0° C., and stir for an additional 15 hat 23° C. Add NaHCO$_3$ (sat.) (150 mL) and extract with CH$_2$Cl$_2$ (150 mL×2), wash the combined organic layer with brine and concentrate to give 35.5 g product.

Step 2: Dissolve the product of Step 1 (7 g, 21 mmol) and Et$_3$N (6.37 g, 63 mmol) in CH$_2$Cl$_2$ (200 mL), add chloroacetyl chloride (2.85 g, 25 mmol), and stir for 2 h at 23° C. Add NaHCO$_3$ solution (150 mL) and extract with CH$_2$Cl$_2$ (150 mL×2), wash the combined organic layer with brine and concentrate. Purify by column chromatography, eluting with CH$_2$Cl$_2$ and CH$_3$OH (sat. with NH$_3$) at a ratio of 97:3 to give 5.3 g product.

Step 3: Dissolve the product of Step 2 (5.3 g, 12.0 mmol) in CH$_2$Cl$_2$ with trifluoroacetic acid (15 mL) and stir for 1 h at 23° C. Remove the solvent under reduced pressure and dilute with CH$_2$Cl$_2$ and NaOH (1 M) until pH=10. Extract with CH$_2$Cl$_2$ (150 mL×2), wash the combined organic layer with brine, and concentrate to yield 3.3 g of the title compound.

Preparation 9

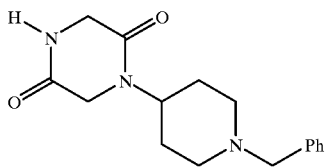

Step 1: Use a procedure similar to Step 1 of Preparation 8, substituting glycine methyl ester hydrochloride for t-butyl-n-(2-aminoethyl)carbamate and HOAc.

Step 2: Treat the product of Step 1 with Boc-glycine using an amidation procedure similar to Step 1 of Example 7A.

Step 3: Treat the product of Step 2 with trifluoroacetic acid using a procedure similar to Step 3 of Preparation 8 to obtain the title compound.

Preparation 10

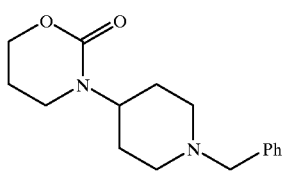

Step 1: Dissolve 4-benzyl-piperidone (11.48 g, 50.7 mmol) in EtOH (60 mL), treat with 3-aminopropanol (8.29 g, 110.4 mmol) and stir for 90 min. Cool to 0° C. and add HCl in dioxane (14 mL, 56 mmol), followed by NaBH$_3$CN (7.8 g, 124 nmol). Allow the mixture to warm up to 23° C., and stir for additional 20 h. Quench with water and dilute with EtOAc, separate the organic layer and basify the aqueous layer until pH>10. Extract the organic layer with EtOAc (2×100 mL), wash the combined organic layer with brine and concentrate. Purify by column chromatography, eluting with CH$_2$Cl$_2$ and CH$_3$OH (sat. with NH$_3$) at a ratio of 94:6 to give 7.5 g product.

Step 2: Treat the product of step 1 using procedure similar to Preparation 3, Step 3, to give 6.6 g of the title compound.

Preparation 11

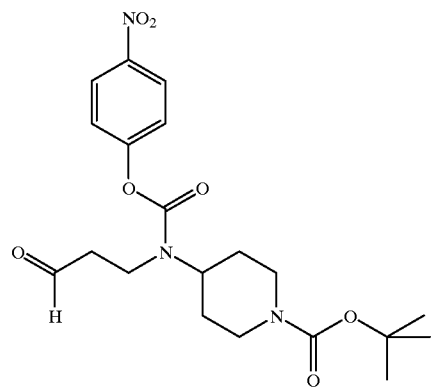

To a 5L 3-neck flask equipped with a mechanical stirring apparatus and charged with 1,2 dichloroethane (400 mL), add N-Boc-piperidone (20 g, 100 mmol, 1 eq) followed by 3-amino-1-propanol (9.21 mL, 120 mmol, 1.2 eq) and stir for 30 min. Add Na(OAc)$_3$BH (25.4 g, 120 mmol, 1.2 eq) and stir for 4 h. Cool reaction to 0° C. and add 300 mL of saturated aqueous NaHCO$_3$. Add p-nitrophenylchloroformate (30.25 g, 150 mmol, 1.5 eq), stir for 90 min and store for 14 h at −20° C. Warm to 0° C. and check for complete reaction by TLC. Prepare a solution of NaBr (11.3 g, 110 mmol, 1.1 eq in 300 mL of saturated aqueous NaHCO$_3$ (sonicate for 5 min)) and add to the reaction vessel. Add TEMPO (156 mg, 1 mmol). With vigorous stirring, use a 500 mL addition funnel to add 300 mL of commercial bleach (ca 0.7 M, 220 mmol, 2.2 eq). If reaction is not complete as shown by TLC, add bleach in small portions (25 mL) until complete. When TLC shows complete reaction, add saturated aqueous Na$_2$S$_2$O$_3$ (300 mL) and transfer to a separatory funnel. Isolate the organic layer and extract the aqueous layer with CH$_2$Cl$_2$ (2×1 L). Combine the organic layers and wash with saturated aqueous NaHCO$_3$ (1 L). Back extract the last aqueous wash with 1 L CH$_2$Cl$_2$, dry over Na$_2$SO$_4$ and concentrate to give 65 g crude product. Purify by silica gel chromatography using 800 g silica, eluting with hexane/EtOAc gradient elution (2:1→1:1) to obtain 36.5 g (87%) of the desired aldehyde.

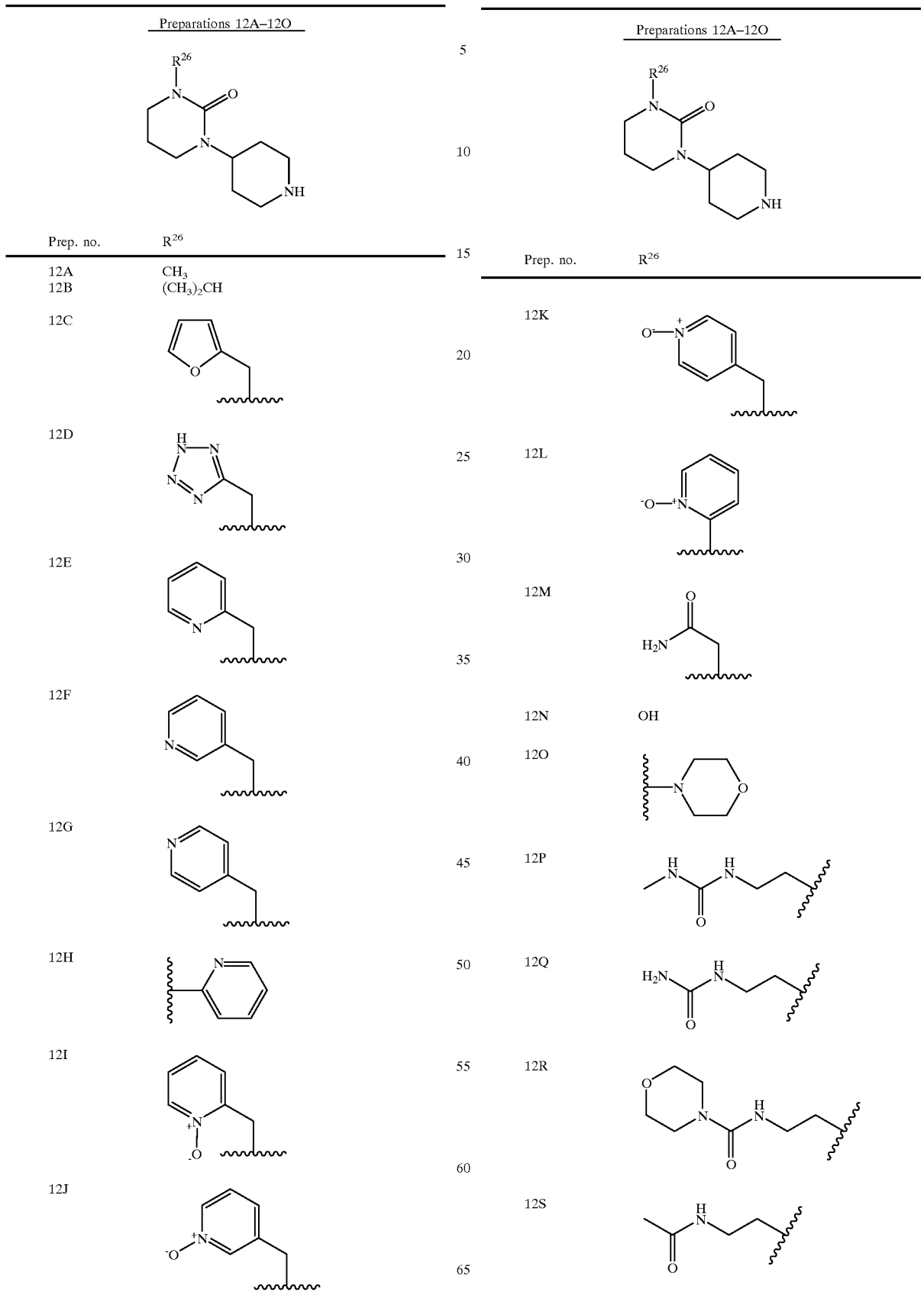

Preparations 12A–12O

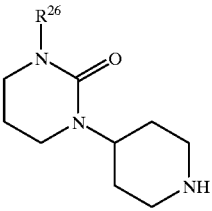

| Prep. no. | R²⁶ |
|---|---|
| 12T | 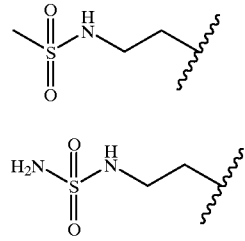 |
| 12U | (H₂N group on sulfonyl version of 12T structure) |

Preparation 12A
Step 1: Using a procedure similar to Preparation 11 with phenyl chloroformate in place of 4-nitrophenylchloroformate, prepare the corresponding phenyl carbamate aldehyde.
Step 2: Stir a solution of the product of step 1 (5 g, 13.2 mmol), $NH_2CH_3$ (7.3 mL of 2M in THF), in 2,2,2-trifluoroethanol (150 mL) for 30 min, then add 4.67 g of $Na(OAc)_3BH$ and stir for 18 h. Filter through a frit, rinse with EtOAc, wash the filtrate with sat $NaHCO_3$ then brine, dry with $Na_2SO_4$ and concentrate in vacuo. Dissolve the crude in DMF (100 mL) and heat to 10 100° C. for 1 h. Remove the DMF in vacuo and purify by silica gel chromatography, eluting with $EtOAc/CH_3OH$ 9:1 to obtain 2.46 g of the desired boc-piperidine.
Step 3: Dissolve the product of step 2 in 30 mL of $CH_2Cl_2$ (30 mL) at 0° C. and treat with 50 mL of HCl/dioxane (4N) and stir until no starting material remains by TLC. Concentrate in vacuo and filter the resulting HCl salt through a plug of silica gel, eluting with $CH_2Cl_2/CH_3OH$ (sat with $NH_3$) to obtain the desired piperidine free base.

Preparation 12B
Using a procedure similar to Preparation 12A, substitute isopropylamine for $NH_2CH_3$ and heat to 125° C. for 6–8 h instead of 100° C. for 1 h in step 2.

Preparation 12C–12H
Step 1: Using a procedure similar to that of Preparation 12A, substituting the product of Preparation 11 for the phenyl carbamate in step 1 and using the appropriate amine, the corresponding Boc-piperidines were prepared. For insoluble amines (Prep. 12D) 1–20% $Et_3N$ was added to 2,2,2 trifluoroethanol as a co-solvent in step 2. In step 2, hindered amines (Prep. 12H) may require sustained heating (120° C., 4–5d) in DMF for cyclization to occur. For less hindered amines, cyclization may be spontaneous and may not require heating in DMF.
Step 2: Deprotect, using a procedure similar to Preparation 12A, step 3.

Preparation 12I–12L
Treat a solution (0.05–0.25 mmol) of the desired Boc protected piperidine obtained from Preparation 12E–12H, step 1, in $CH_2Cl_2$ with 1.5–5 eq mCPBA and stir for 2–18 h. Concentrate in vacuo and purify by silica gel 15 chromatography. Deprotect the Boc group using a procedure similar to that of Preparation 12A, step 3, to give the appropriate piperidine.

Preparation 12M
Using a procedure similar to Preparations 12C–H, steps 1 and 2, substituting glycineamide for the appropriate amine, the resulting glycineamide substituted urea/piperidine free base is prepared.

Preparation 12N
Step 1: Treat a solution of the product of Preparation 12A, step 1 (6.2 g, 16.5 mmol) in pyridine (100 mL) with $NH_2OH$ (1.72 g, 24.7 mmol) and heat to 60° C. for 2.5 h. Cool and concentrate in vacuo and purify by silica gel 25 chromatography, eluting with $CH_2Cl_2/CH_3OH$ ($NH_3$) to obtain 5.9 g (88%) of the oxime as a white powder.
Step 2: Treat a solution of the product of step 1(5.7 g, 15 mmol) in 170 mL $CH_3OH$ with a trace amount of methyl orange indicator followed by $NaCNBH_3$ (1.03 g). Add 1 M $HCl/CH_3OH$ until mixture remains orange (ca. 23 mL). Quench with 400 mL EtOAc and 75 mL sat $NaHCO_3$. Filter the resulting emulsion through celite and wash with EtOAc. Wash organic layers with 75 mL saturated $NaHCO_3$, then brine, dry over $Na_2SO_4$ and concentrate in vacuo to obtain 3.82 g (67%) of the hydroxyl amine as a colorless glass.
Step 3: Dissolve the product of step 2 in 50 mL DMF and heat to 100° C. for 4 h. Concentrate in vacuo and purify by silica gel chromatography using $CH_2Cl_2/CH_3OH$ ($NH_3$) to obtain 3.0 g (99%) of the hydroxyl urea.
Step 4: In a procedure similar to Preparation 12A, step 3, deprotect the Boc group to obtain the desired piperidine.

Preparation 12O
Step 1: Treat a solution of the product of Preparation 12A, step 1 (3.0 g, 7.13 mmol) in 1,2-dichloroethane (20 mL) with aminomorpholine (1.37 mL, 14.25 mmol) and $Na(OAc)_3BH$ (3.0 g). Isolate the resulting hydrazone by filtering the reaction mixture through a frit and concentrating in vacuo.
Step 2: Treat a solution of the product of step 1 in 50 mL THF with 1 eq of tosic acid followed by $NaCNBH_3$ (2 eq). Quench with sat. $NaHCO_3$ and extract with EtOAc. Wash the organic layers with saturated $NaHCO_3$, then brine, dry over $Na_2SO_4$ and concentrate in vacuo. Purify by silica gel chromatography, eluting with EtOAc/hexane (2:1) with 2% $Et_3N$ to obtain 1.5 g of the desired hydrazone.
Step 3: Dissolve the product of step 2 in 50 mL DMF and heat to 120° C. for 3 h. Concentrate in vacuo and purify by silica gel chromatography, eluting with $CH_2Cl_2/CH_3OH$ ($NH_3$) to obtain 255 mg (10%, 2 steps) of the aminomorpholino urea.
Step 4: In a procedure similar to Preparation 12A, step 3, deprotect the Boc group to obtain the desired piperidine.

Preparation 12P
Step 1: Using a procedure similar to Preparation 12A, Step 2, substitute aminoacetonitrile for methyl amine. Dissolve the product in $CH_3OH$, add Raney Ni, and shake the resulting mixture on a Parr shaker at 50 psi of $H_2$ pressure for 3 h. Filter the mixture through celite and concentrate to give the desired product.
Step 2: Dissolve the product of Step 1 (0.17 g, 0.52 mmol) in $CH_2Cl_2$ and treat with methyl isocyanate (0.035 ml, 0.57 mmol) at 23° C. for 3 h. Dilute with water and CH₂Cl₂ separate the layers, and extract the aqueous layer with CH₂Cl₂ (2×40 ml), wash the combined organic layers with brine and 30 concentrate. Purify by column chromatography using CH₂Cl₂ and CH₃OH (sat. with ammonia) at a ratio of 98:2 to give 0.68 g of product.
Step 3: Use a procedure similar to Preparation 12A, Step 3, to give the desired product.

Preparation 12Q–12T

Using a procedure similar to Preparation 12B, substitute for methyl isocyanate the appropriate isocyante or chloride.

Preparation 12U
Step 1: Dissolve the product form Preparation 12P, Step 1, in dioxane, treat with sulfamide, reflux at 100° C. for 8 h, and concentrate to give a crude product.
Step 2: Use a procedure similar to Preparation 12A, Step 3, to give the desired product.

EXAMPLE 1

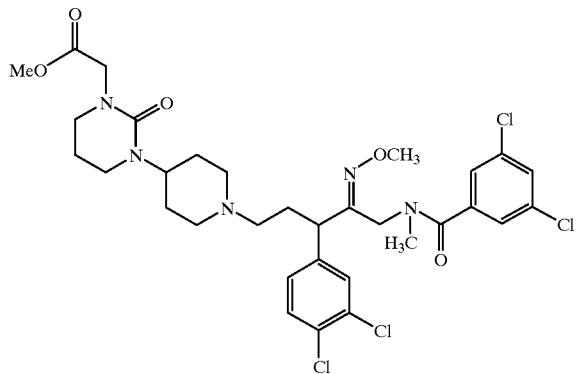

Step 1: Dissolve product of Preparation 3 (11.3 g, 0.042 mol) in anhydrous dimethylformamide (DMF) (30 mL), treat it with lithium bis(trimethylsilyl)amide (1 M, 50 mL, 0.050 mol) at 0° C., allow the reaction mixture to warm up to 23° C. over 40 min. Add t-butyl bromoacetate (13.5 mL, 0.084 mol), and stir for 18 h. Quench with water and dilute with ethyl acetate (EtOAc), separate the organic layer, concentrate and purify the mixture by column chromatography eluting with CH₂Cl₂ and CH₃OH (sat. with NH₃) at a ratio of 98:2 to give 12.1 g product.
Step 2: Bubble HCl into a solution of the product of Step 1 (12.2 g, 0.032 mol) in CH₃OH (200 mL) for 15 min at 0° C. and heat the resulting solution at 60° C. for 2 h. After cooling, pour the reaction mixture into 10% aqueous NaOH solution (100 mL) and add NaHCO₃ solution (sat.) until pH=10. Separate the organic layer and further extract the aqueous layer with CH₂Cl₂ (2×100 mL), wash the combined organic layer with brine and concentrate to yield 12.3 g product.
Step 3A: Dissolve the product of Step 2 (1 g, 3.0 mmol) in CH₃OH (10 mL) add Pd(OH)2 on carbon (150 mg), and shake the resulting mixture on a Parr shaker at 50 psi of H₂ pressure for 3 h. Filter the mixture through celite and concentrate to give a crude product. Re-dissolve the product and the aldehyde from Preparation 1 (1.5 g, 3.14 mmol) in trifluoroethanol (10 mL), treat with 3A molecular sieves (0.3 g) and NaBH₃CN (0.37 g, 6.0 mmol), and stir for 2 h. Add water (30 mL) and EtOAc (30 mL), filter the mixture through celite, separate layers of filtrate, extract the aqueous solution with EtOAc (2×40 mL), and concentrate the combined organic layer. Purify by column chromatography, eluting with CH₂Cl₂ and CH₃OH (sat. with NH₃) at a ratio of 98:2 to give 0.89 g of desired product. HRMS (FAB, M+H⁺): Calc'd: 714.1784, found: 714.1791.
Step 3B: Alternatively, to prepare optically active material, proceed in a similar manner as Step 3A using the aldehyde from Preparation 2 in place of the aldehyde from Preparation 1, dichloroethane in place of trifluoroethanol, and sodium triacetoxyborohydride in place of NaBH₃CN. HRMS (FAB, M+H⁺): Calc'd: 714.1784, found: 714.1779.

EXAMPLE 2

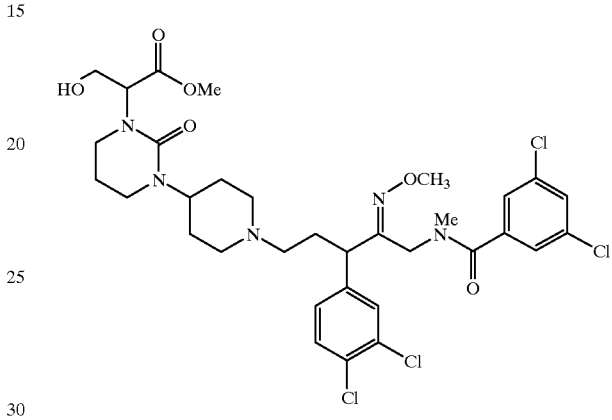

Step 1: Using a procedure similar to Preparations 12C–H, steps 1 and 2, and substituting serine methyl esters•HCl for the appropriate amine, the resulting serine methyl ester substituted urea/piperidine free base is prepared.
Step 2: Treat the product of step 1 (3.68 mmol) in 1,2 dichloroethane (20 mL and 5 mL CF₃CH₂OH) with Preparation 2 (1.23 g, 2.45 mmol) and 3Å MS (1.5 g). Stir for 30 min, then add Na(OAc)₃BH (943 mg, 4.5 mmol) and stir for 1–5 h. Filter through celite and wash the celite pad with EtOAc. Transfer to a separatory funnel and wash with sat NaHCO₃ (2×50 mL) then brine, dry the organic layer with Na₂SO₄ and concentrate in vacuo. Purify by chromatography (EtOAc/NEt₃) to obtain 1.3 g of the desired product.

EXAMPLE 3

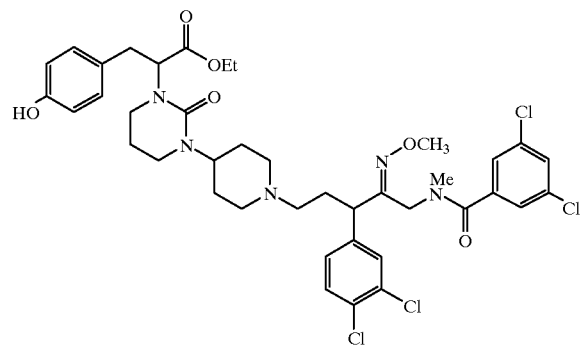

Use a procedure similar to Example 2, substituting tyrosine ethyl esters•HCl for serine methyl esters•HCl to obtain the product.

EXAMPLE 4

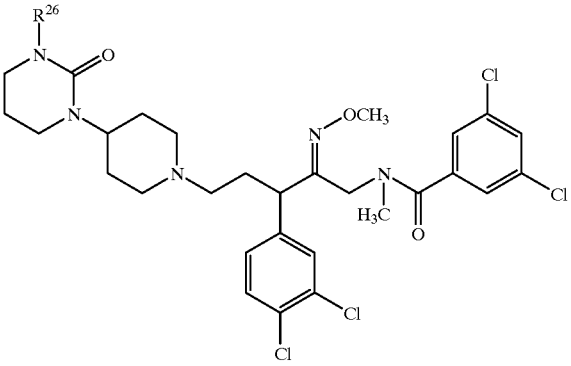

| Ex. | R²⁶ | HRMS (FAB, M + H⁺) |
|---|---|---|
| 4A | HOOC-CH₂CH₂- | Calc'd: 700.1627, found: 700.1619 |
| 4B | pyrrolidinyl-C(O)-CH₂CH₂- | Calc'd: 753.2256 found: 753.2248 |
| 4C | (CH₃)₂N-C(O)-CH₂CH₂- | Calc'd: 727.2100, found: 727.2120 |
| 4D | CH₃NH-C(O)-CH₂CH₂- | Calc'd: 713.1943, found: 713.1937 |
| 4E | H₂N-C(O)-CH₂CH₂- | Calc'd: 699.1787, found: 699.1784 |
| 4F | morpholino-C(O)-CH₂CH₂- | Calc'd: 769.2206, found: 769.2207 |
| 4G | 4-methylpiperazinyl-C(O)-CH₂CH₂- | Calc'd: 782.2522, found: 782.2514 |
| 4H | thiomorpholinyl(O)ₙ-C(O)-CH₂CH₂- (n = 0, 2) | n = 1 Calc'd: 785.1977, found: 785.1974  n = 2 Calc'd: 817.1875, found: 817.1862 |
| 4I | thiazol-2-yl-NH-C(O)-CH₂CH₂- | Calc'd: 782.1617 found: 782.1624 |
| 4J | 1,3,4-thiadiazol-2-yl-NH-C(O)-CH₂CH₂- | Calc'd: 783.1569 found: 783.1570 |
| 4K | EtO-C(O)-CH₂CH₂- | Calc'd: 728.1940, found: 728.1930 |
| 4L | F₃C-CH₂-O-C(O)-CH₂CH₂- | Calc'd: 782.1657 found: 782.1662 |
| 4M | (CH₃)₂N-CH₂CH₂-O-C(O)-CH₂CH₂- | Calc'd: 771.2362 found: 771.2350 |
| 4N | Ph-CH₂-O-C(O)-CH₂CH₂- | Calc'd: 790.2097 found: 790.2103 |

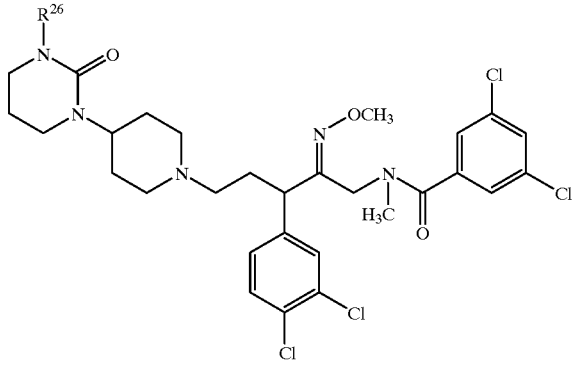

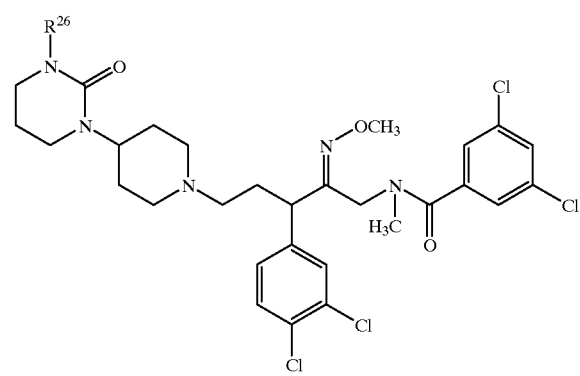

| Ex. | R²⁶ | HRMS (FAB, M + H⁺) |
|---|---|---|
| 4O | 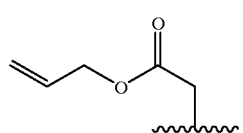 | Calc'd: 740.1940<br>found: 740.1943 |
| 4P | 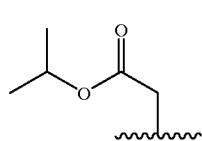 | Calc'd: 742.2097<br>found: 768.2091 |
| 4Q | 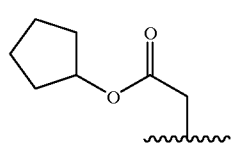 | Calc'd: 768.2253<br>found: 768.2235 |
| 4R | 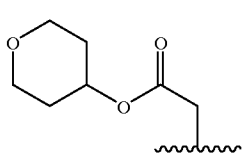 | Calc'd: 784.2202<br>found: 784.2198 |
| 4S | 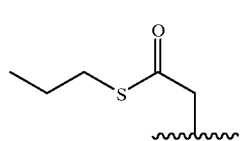 | Calc'd: 758.1868<br>found: 782.1862 |
| 4T | 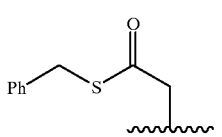 | Calc'd: 806.1868<br>found: 806.1853 |
| 4U | 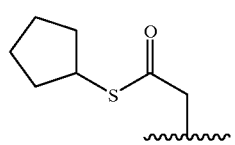 | Calc'd: 784.2025<br>found: 784.2022 |

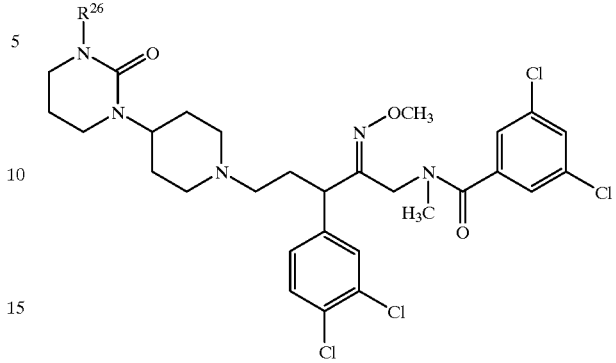

| Ex. | R²⁶ | HRMS (FAB, M + H⁺) |
|---|---|---|
| 4V | 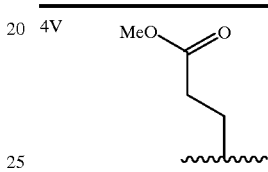 | Calc'd: 728.1940,<br>found: 728.1932 |
| 4W | 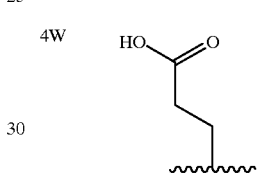 | Calc'd: 714.1784,<br>found: 714.1776 |
| 4X | 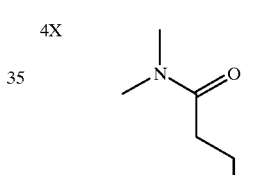 | Calc'd: 741.2256,<br>found: 741.2247 |
| 4Y | OH 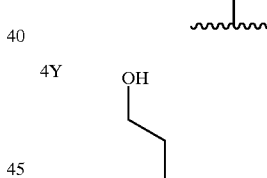 | Calc'd: 686, 1834<br>found 686.1855 |
| 4Z | OMe 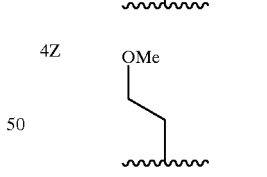 | Calc'd: 700.1991<br>found: 700.1984 |
| 4ZZ | 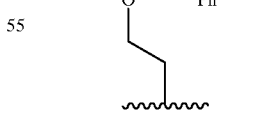 | Calc'd: 776.2304<br>found: 776.2302 |

EXAMPLE 4A

Dissolve the product of Step 3A of Example 1 (0.50 g, 0.69 mmol) in $CH_3OH$ (6 mL), add a solution of NaOH (60 mg, 1.5 mmol) in water (0.25 mL), and stir for 4 h. Add an equivalent of HCl (10% in water) and extract the mixture with 15% $CH_3OH$ in $CH_2Cl_2$ (5×30 mL). Concentrate the combined organic layer and purify by column chromatography using 15% CH$_3$OH in CH$_2$Cl$_2$ to give 0.36 g of the desired product.

EXAMPLE 4B

Dissolve the product of Example 4A (60 mg, 0.086 mmol) and carbonyldiimidazole (28 mg, 0.17 mmol) in CH$_2$Cl$_2$ (1 mL), and add pyrrolidine (22 mL, 0.26 mmol) at 0° C. After stirring at 23° C. for 12 h, add water (20 mL) and CH$_2$Cl$_2$ (20 mL), separate the layers, extract the aqueous layer with CH$_2$Cl$_2$ (2×20 mL), wash the combined organic layer with brine, concentrate, and purify the mixture with column chromatography eluting with CH$_2$Cl$_2$ and CH$_3$OH with NH$_3$ (98:2) to give 47 mg of the product.

EXAMPLES 4C–4J

Prepare the compounds by reacting the product of Example 4A with an appropriate amine according to procedure similar to Example 4B.

EXAMPLE 4K

Dissolve the product of Example 4A (200 mg, 0.29 mmol), 1,3-dicyclohexylcarbodiimide (DCC) (87 mg, 0.43 mmol) and 4-dimethylaminopyridine (DMAP) (53 mg, 0.43 mmol) in CH$_2$Cl$_2$ (2 mL), add EtOH (25 mL, 0.43 mmol) at 0° C. After stirring at 23° C. for 12 h, add water (20 mL) and CH$_2$Cl$_2$ (20 mL), separate the layers, extract the aqueous layer with CH$_2$Cl$_2$ (2×20 mL), wash the combined organic layer with brine, concentrate and purify the mixture with column chromatography eluting with CH$_2$Cl$_2$ and CH$_3$OH with NH$_3$ (97:3) to give 165 mg of the product.

EXAMPLES 4L–4R

Prepare the target compounds by reacting the product of Example 4A with an appropriate alcohol according to a procedure similar to Example 4K.

EXAMPLES 4S–4T

Prepare the compounds using a procedure similar to Example 4K, using bis(2-oxo-3-oxazolidinyl)phosphinic chloride (BOP-Cl), Et$_3$N and appropriate thiols in place of DCC, DMAP and EtOH.

EXAMPLE 4V

Use a procedure similar to Example 1, Step 1, using methyl 3-bromopropionate in place of t-butyl bromoacetate, followed by debenzylation and reductive amination using a procedure similar to Example 1, Step 3.

EXAMPLE 4W

Treat the product of Example 4Y using a hydrolysis procedure similar to that of Example 4A.

EXAMPLE 4X

Treat the product of Example 4W using an amidation procedure similar to Example 4B using (CH$_3$)$_2$NH in place of pyrrolidine.

EXAMPLE 4Y

1) Dissolve the product of Preparation 11 (19 g, 44 mmol) and ethanolamine (4 mL, 66 mmol) in dichloroethane (120 mL) and stir for 30 min. Treat with sodium triacetoxyborohydride (14 g, 66 mmol) and stir for 14 h. Add NaHCO$_3$ (sat.) (150 mL), extract with CH$_2$Cl$_2$ (150 mL×2), wash the combined organic layer with brine and concentrate to give 8.75 g product. 2) Treat the product of Step 1 by a procedure similar to Example 1, Step 3A, to give the product.

EXAMPLE 4Z

Dissolve the product of Example 4Y (138 mg, 0.2 mmol) in dry THF (1 mL), add NaH (16 mg, 0.4 mmol) at 0° C. and stir for 15 min. Add CH$_3$I (19 mL, 0.3 mmol) at 0° C., allow the mixture to warm to 23° C., and stir for 2 h. Quench the reaction at 0° C. with water (10 mL) and dilute with EtOAc (10 mL). Separate the layers, extract aqueous solution with EtOAc (2×40 mL) and concentrate the combined organic layer. Purify by column chromatography using EtOAc and CH$_3$OH (99:1) with 5% Et$_3$N to give 103 mg product.

EXAMPLE 4ZZ

Treat the product of Example 4Y using a procedure similar to Example 4Z substituting benzyl bromide for CH$_3$I.

EXAMPLE 5

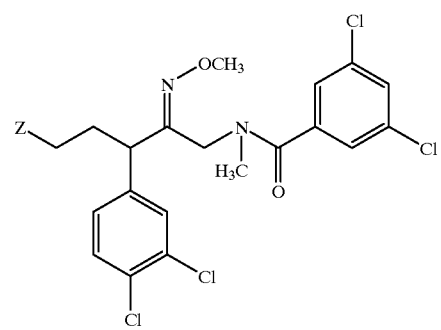

| Ex. | Z | HRMS (FAB, M + H$^+$) |
|---|---|---|
| 5A | 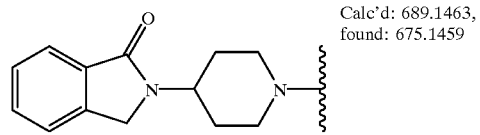 | Calc'd: 689.1463, found: 675.1459 |
| 5B | 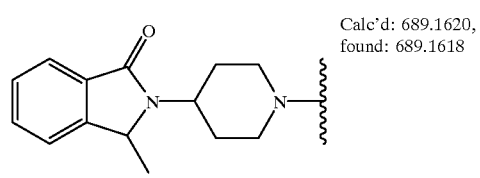 | Calc'd: 689.1620, found: 689.1618 |
| 5C | 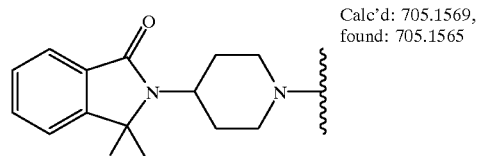 | Calc'd: 705.1569, found: 705.1565 |

EXAMPLES 5A–5C

Prepare the compounds by a procedure similar to Example 1, Step 3, using the products of Preparations 4, 5 and 6, respectively.

EXAMPLE 6

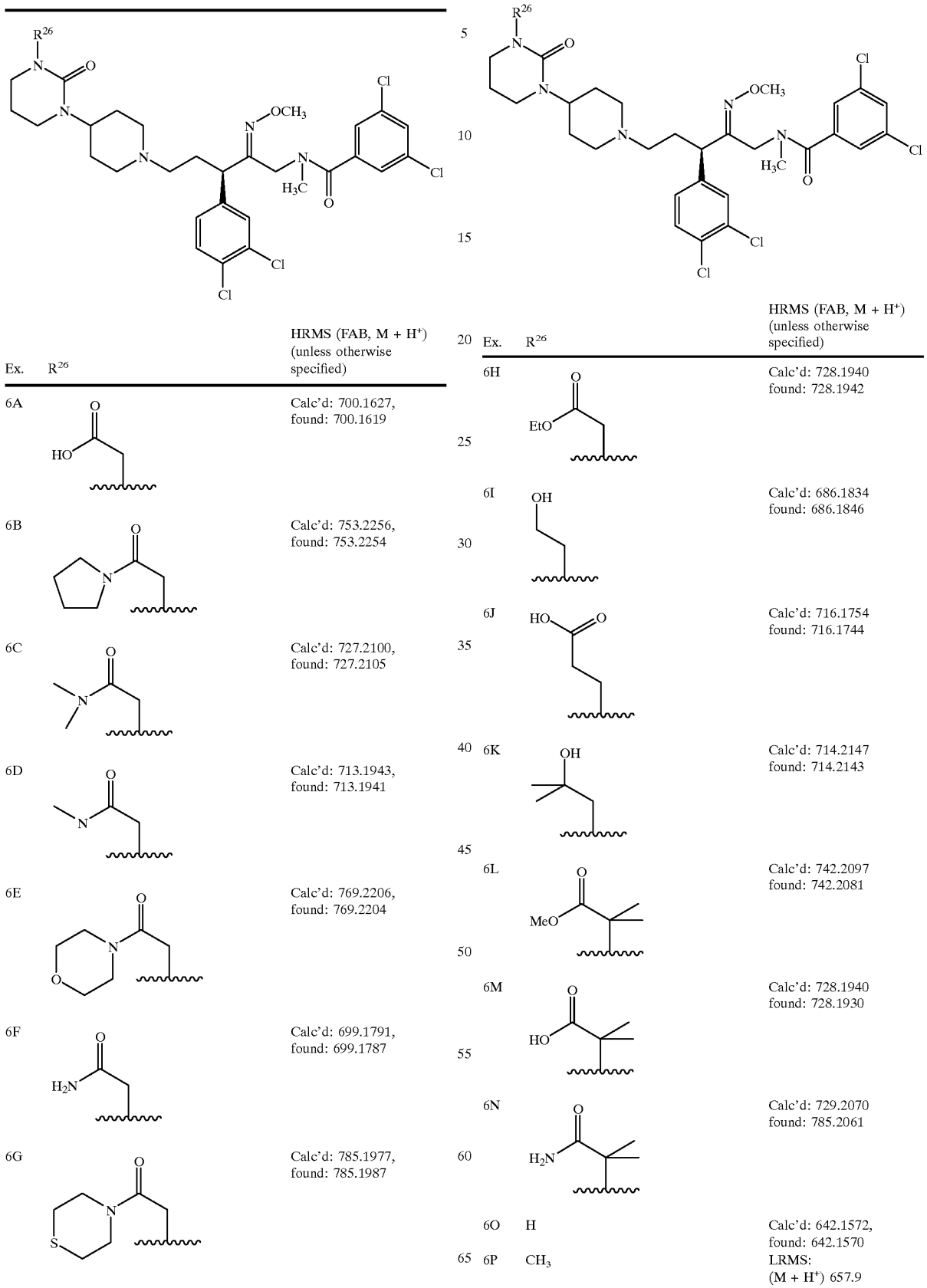

| Ex. | R²⁶ | HRMS (FAB, M + H⁺) (unless otherwise specified) |
|---|---|---|
| 6A | HO-C(=O)-CH₂-CH₂- | Calc'd: 700.1627, found: 700.1619 |
| 6B | pyrrolidinyl-C(=O)-CH₂-CH₂- | Calc'd: 753.2256, found: 753.2254 |
| 6C | (CH₃)₂N-C(=O)-CH₂-CH₂- | Calc'd: 727.2100, found: 727.2105 |
| 6D | CH₃NH-C(=O)-CH₂-CH₂- | Calc'd: 713.1943, found: 713.1941 |
| 6E | morpholinyl-C(=O)-CH₂-CH₂- | Calc'd: 769.2206, found: 769.2204 |
| 6F | H₂N-C(=O)-CH₂-CH₂- | Calc'd: 699.1791, found: 699.1787 |
| 6G | thiomorpholinyl-C(=O)-CH₂-CH₂- | Calc'd: 785.1977, found: 785.1987 |
| 6H | EtO-C(=O)-CH₂-CH₂- | Calc'd: 728.1940, found: 728.1942 |
| 6I | HO-CH₂-CH₂-CH₂- | Calc'd: 686.1834, found: 686.1846 |
| 6J | HO-C(=O)-CH₂-CH₂-CH₂- | Calc'd: 716.1754, found: 716.1744 |
| 6K | HO-C(CH₃)₂-CH₂- | Calc'd: 714.2147, found: 714.2143 |
| 6L | MeO-C(=O)-C(CH₃)₂-CH₂- | Calc'd: 742.2097, found: 742.2081 |
| 6M | HO-C(=O)-C(CH₃)₂-CH₂- | Calc'd: 728.1940, found: 728.1930 |
| 6N | H₂N-C(=O)-C(CH₃)₂-CH₂- | Calc'd: 729.2070, found: 785.2061 |
| 6O | H | Calc'd: 642.1572, found: 642.1570 |
| 6P | CH₃ | LRMS: (M + H⁺) 657.9 |

-continued
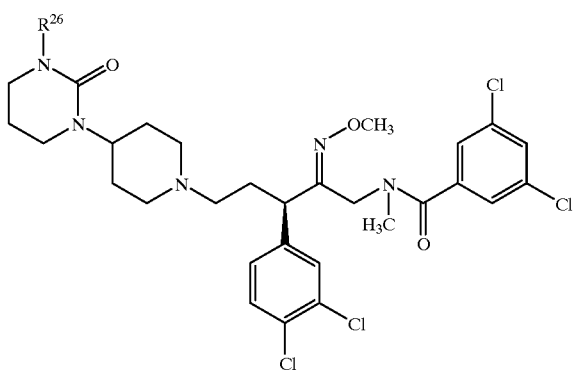
| Ex. | R²⁶ | HRMS (FAB, M + H⁺) (unless otherwise specified) |
|---|---|---|
| 6Q | (CH₃)₂CH— | LRMS: (M + H⁺) 687.0 |
| 6R | 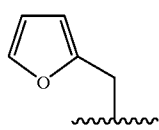 | Calc'd: 722.1834, found: 722.1832 |
| 6S | 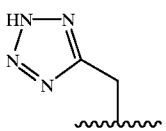 | Calc'd: 724.1852, found: 724.1879 |
| 6T | 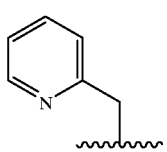 | LRMS: (M + H⁺) 735.2 |
| 6U | 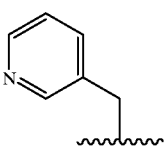 | LRMS: (M + H⁺) 735.2 |
| 6V | 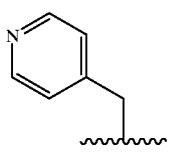 | LRMS: (M + H⁺) 735.2 |
| 6W | 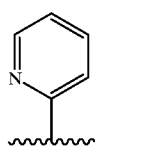 | Calc'd: 719.1838, found: 719.1849 |
-continued
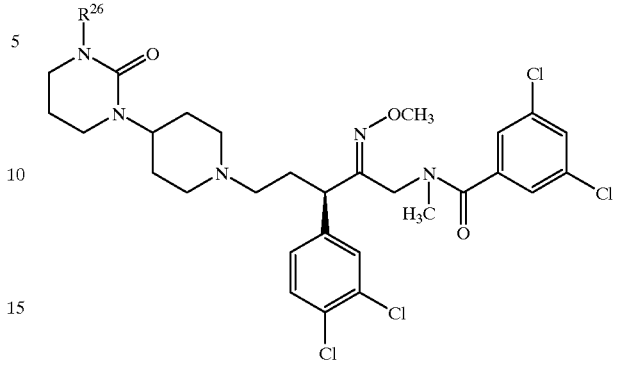
| Ex. | R²⁶ | HRMS (FAB, M + H⁺) (unless otherwise specified) |
|---|---|---|
| 6X | 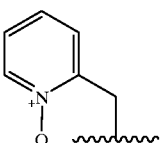 | LRMS: (M + H⁺) 751.2 |
| 6Y | 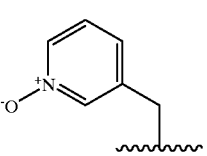 | Calc'd: 749.1943, found: 749.1922 |
| 6Z | 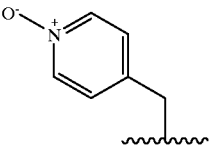 | Calc'd: 749.1943, found: 749.1937 |
| 6AA | 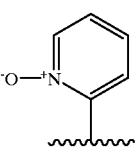 | Calc'd: 735.1787, found: 735.1800 |
| 6BB | 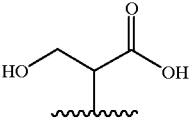 | Calc'd: 730.1733, found: 730.1733 |
| 6CC | 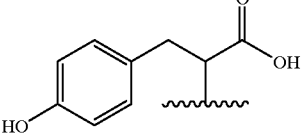 | Calc'd: 806.2046, found: 806.2034 |
| 6DD | 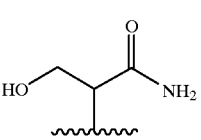 | LRMS: (M + H⁺) 731.1 |

-continued

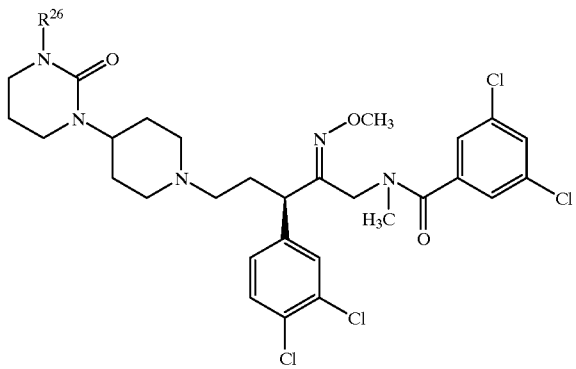

| Ex. | R²⁶ | HRMS (FAB, M + H⁺) (unless otherwise specified) |
|---|---|---|
| 6EE | 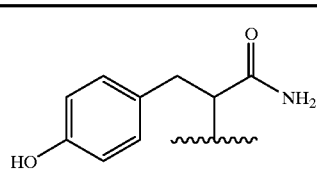 | LRMS: (M + H⁺) 807.2 |
| 6FF | 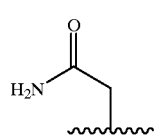 | Calc'd: 699.1787, found: 699.1791 |
| 6GG | 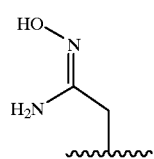 | Calc'd: 714.1898, found: 714.1891 |
| 6HH | 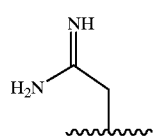 | Calc'd: 698.1967, found: 698.1959 |
| 6II | OH | Calc'd: 660.1492, found: 660.1487 |
| 6JJ | 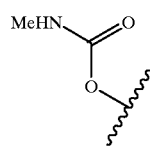 | LRMS: (M + H⁺) 660.2 |
| 6KK | 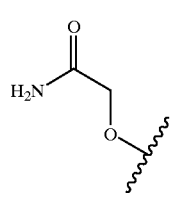 | LRMS: (M⁺) 717.2 |

-continued

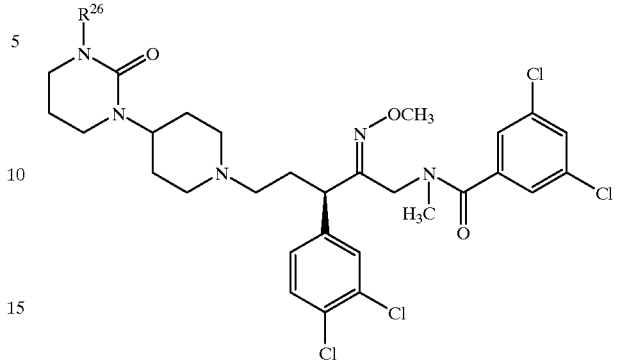

| Ex. | R²⁶ | HRMS (FAB, M + H⁺) (unless otherwise specified) |
|---|---|---|
| 6LL | 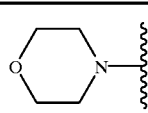 | Calc'd: 727.2100, found: 727.2114 |
| 6MM | 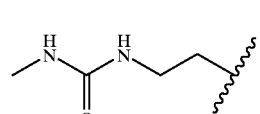 | Calc'd: 742.2209, found: 742.2199 |
| 6NN | 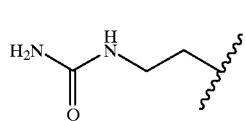 | LRMS: (M + H⁺) 730 |
| 6OO | 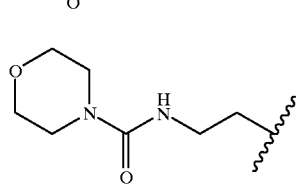 | LRMS: (M + H⁺) 800 |
| 6PP | 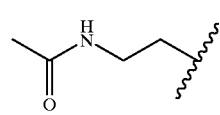 | Calc'd: 729.2070, found: 729.2052 |
| 6QQ | 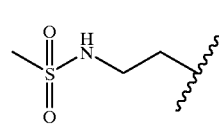 | Calc'd: 765.1740, found: 765.1747 |
| 6RR | 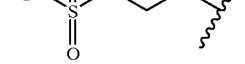 | Calc'd: 766.1693, found: 766.1685 |

EXAMPLE 6A

Prepare the compound by a procedure similar to Example 4A using product of Example 1, Step 3B in place of the product of Example 1, Step 3A.

EXAMPLES 6B–6G

Treat the product of Example 6A with appropriate amines using an amidation procedure similar to Example 4B using 1-(3-dimethylamino-propyl-3-ethylcarbodiimide (EDC) and 1-hydroxybenzotriazole (HOBt) in place of carbonyldiimidazole.

EXAMPLES 6H–6J

Prepare the compounds by procedures similar to Examples 4K, 4Y and 4W, except using the optically pure product from Preparation 2 in place of product of Preparation 1.

EXAMPLE 6K

Dissolve the product of Example 6H (0.12 g, 0.16 mmol) in anhydous THF (2 mL) and add $CH_3MgBr$ (3 M, 0.2 mL, 0.6 mmol) at 0° C. Warm the mixture and stir at 23° C. for 3 h. Add water and $CH_2Cl_2$ at 0° C., separate the layers, extract the aqueous layer with $CH_2Cl_2$ (2×40 mL), wash the combined organic layer with brine and concentrate. Purify by column chromatography eluting with $CH_2Cl_2$ and $CH_3OH$ (99:1 to 95:5) to give 0.05 g of the product.

EXAMPLE 6L

Step 1: Use the procedure in Preparation 11, substituting N-benzyl piperidone for N-Boc-piperidone, and substituting a standard Swern oxidation for TEMPO oxidation.
Step 2: Dissolve the product of Step 1 (6.83 g, 16.6 mmol) and α,α-dimethyl glycine methyl ester hydrochloride (2.86 g, 18.6 mmol) in trifluoroethanol (32 mL) and $CH_2Cl_2$ (63 mL), add $NaSO_4$ (2.8 g) and stir for 30 min. Treat the mixture with sodium triacetoxy borohydride and stir for additional 4 h. Filter off the solid and concentrate to yield the crude product. Purify by column chromatography eluting with EtOAc and $CH_3OH$ (99:1 to 95:5) to give 7.65 g product.
Step 3: Dissolve the product of Step 2 (1.54 g, 3 mmol) in toluene (140 mL) and heat in a sealed tube at 120° C. for 40 h. Cool and remove the solvent, re-dissolve in EtOAc and $CH_2Cl_2$, wash with 1 N NaOH, brine and concentrate to yield 0.97 g product.
Step 4: Treat the product in Step 3 using a procedure similar to Preparation 3, Step 3, to give the product.

EXAMPLE 6M

Step 1: Treat the product of Step 3 of Example 6L with a hydrolysis procedure similar to Example 6A, but reflux at 70° C. for 24 h.
Step 2: Treat the pro'duct of Step 1 using a procedure similar to Example 1, Step 3 to give the product.

EXAMPLE 6N

Treat the product of Example 6M with an amidation procedure similar to Example 4E to give the product.

EXAMPLE 6O

Step 1: Dissolve the product of Preparation 3, step 3 (2.0 g, 7.5 mmol) in $CH_3OH$ (50 mL) and treat with $Pd(OH)_2$ (20% on C, 50% $H_2O$) followed by $H_2$ (40 psi). After shaking for 17 h on Parr shaker, filter through celite and concentrate to obtain the desired piperidine (1.33 g, 7.3 mmol, 98%).
Step 2: Treat the product of step 1 (2.13 g, 4.5 mmol) in 1,2-dichloroethane 10 (15 mL) with Preparation 2 (1.42 g, 3.0 mmol) and 3ÅMS (2 g). Stir for 30 min and then add $Na(OAc)_3BH$ (943 mg, 4.5 mmol) and stir for 1–5 h. Filter through celite and wash the celite pad with EtOAc. Transfer to a separatory funnel, wash with sat $NaHCO_3$ (2×50 mL), brine and dry the organic layer with $Na_2SO4$ and concentrate in vacuo. Purify by chromatography (EtOAc/$NEt_3$→EtOAc/ $NEt_3$/$CH_3OH$ gradient) to obtain 810 mg of the desired product.

Examples 6P through 6AA, 6FF, 6II, and 6LL–6RR

Use the appropriate piperidine from Preparation 12A through 12L, 12M, 12N, and 12O–12U and the aldehyde from Preparation 2 in a procedure similar to example 60, step 2 to obtain the title compounds.

EXAMPLE 6BB

Use the product of Example 2 in a procedure similar to Example 4A to obtain the corresponding carboxylic acid compound.

EXAMPLE 6CC Use the product of Example 3 in a procedure similar to Example 4A substituting LiOH for NaOH and aqueous DME for $CH_3OH$ to obtain the corresponding carboxylic acid title compound.

EXAMPLES 6DD and 6EE

With Examples 6BB and 6CC as the starting carboxylic acids, use a procedure similar to Example 4K using HOBT in place of DMAP and using $NH_3$ in THF as the amine to obtain Examples 6DD and 6EE, respectively.

EXAMPLE 6GG

Step 1: Cool a suspension of dry $NH_4Cl$ (58 mg) in benzene (5 mL) to 0° C. and treat with 525 µL of 2M trimethylaluminum in toluene. Warm to 23° C. 35 and stir for 1 h. Add 250 mg of example 6FF and heat the mixture to reflux for 2.5 h. Cool and remove the solvent in vacuo and purify the resulting nitrile by silica gel chromatography using $CH_2Cl_2$/$CH_3OH$ ($NH_3$) (95:5) as the eluant to obtain 140 mg (57%) of the nitrile.
Step 2: Sonicate a mixture of $NH_2OH$ (152 mg, 2.21 mmol) in dry EtOH (5 mL) and 1 N KOH/$CH_3OH$ (1.76 mL) for 15 min. Add this suspension to a solution of the product of step 1 (300 mg) in dry EtOH (7 mL) with 3ÅMS and heat to reflux for 2 h. Quench with saturated $NaHCO_3$, dilute with EtOAc (150 mL), filter through a frit and concentrate in vacuo. Purify by silica gel chromatography using $CH_2Cl_2$/$CH_3OH$ ($NH_3$) (97:3→95:5) to obtain the title compound.

EXAMPLE 6HH

Treat a solution of the product of Example 6GG, step 1 (300 mg) in $CH_3OH$ (5 mL) with 47 mg of $NaOCH_3$ and stir for 18 h at 23° C. Add dry $NH_4Cl$ and stir for 4 h. Remove the solvent in vacuo and purify by silica gel chromatography using $CH_2Cl_2$/$CH_3OH$ ($NH_3$) (95:5→80:10) to obtain 262 mg (86%) of the title compound.

EXAMPLE 6JJ

Treat a solution of example 6II (250 mg, 0.38 mol) and 46 µL (0.57 mmol) of pyridine in 3 mL $CH_2Cl_2$ with methylisocyanate (33.5 µL, 0.57 mmol) and stir for 3 h. Remove the solvent in vacuo and purify by silica gel chromatography using $CH_2Cl_2$/$CH_3OH$ ($NH_3$) (95:5) to obtain 226 mg (83%) of the title compound.

EXAMPLE 6KK

Step 1: Treat a solution of Example 6II (500 mg, 0.76 mol) in dry DMF (10 mL) at 0° C. with NaH (46 mg, 60%) and stir for 30 min. Add methylbromoacetate (86 µL, 0.914 mmol) stir for 30 min and quench with 3 mL saturated $NaHCO_3$. Extract with EtOAC, filter through a frit, wash with saturated $NaHCO_3$, brine, dry with $Na_2SO_4$ and concentrate in vacuo. Purify by silica gel chromatography using $CH_2Cl_2$/$CH_3OH$ ($NH_3$) (97:3) to obtain 440 mg (79%) of the methyl ester.

Step 2: Treat a solution of the product of step 1 (389 mg) with CH$_3$OH saturated with NH$_3$ (20 mL) and sonicate for 2 h. Concentrate in vacuo. Purify by silica gel chromatography using CH$_2$Cl$_2$/CH$_3$OH (NH$_3$) (95:5) to obtain 300 mg (79%) of the title compound.

EXAMPLE 7

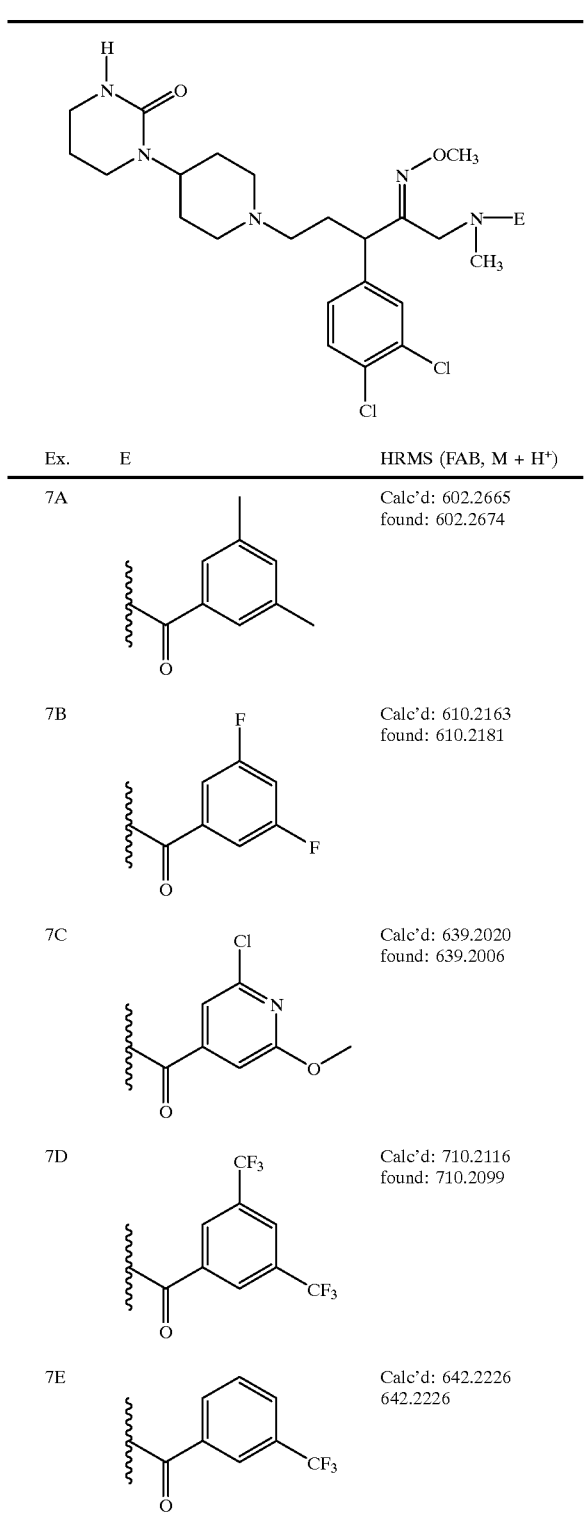

| Ex. | E | HRMS (FAB, M + H$^+$) |
|---|---|---|
| 7A | | Calc'd: 602.2665<br>found: 602.2674 |
| 7B | | Calc'd: 610.2163<br>found: 610.2181 |
| 7C | | Calc'd: 639.2020<br>found: 639.2006 |
| 7D | | Calc'd: 710.2116<br>found: 710.2099 |
| 7E | | Calc'd: 642.2226<br>642.2226 |

-continued

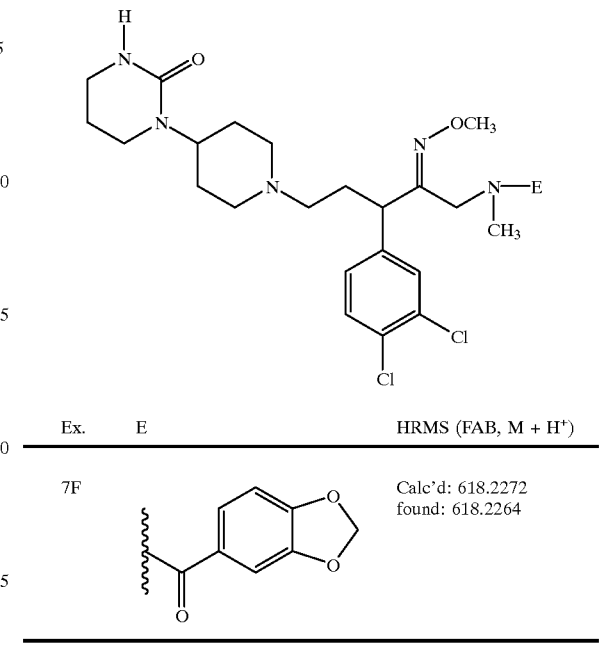

| Ex. | E | HRMS (FAB, M + H$^+$) |
|---|---|---|
| 7F | | Calc'd: 618.2272<br>found: 618.2264 |

EXAMPLE 7A

Step 1: Dissolve the product of Preparation 7 (1.0 g, 1.36 mmol), EDC (0.38 g, 2.00 mmol) and HOBt (0.24 g, 1.8 mmol) in CH$_2$Cl$_2$ (5 mL), add 3,5-dimethyl benzoic acid (0.3 g, 2.00 mmol) and Et$_3$N (0.7 mL, 4.00 mmol) at 0° C. After stirring at 23° C. for 12 h, add water (20 mL) and CH$_2$Cl$_2$ (20 mL), separate the layers, extract the aqueous layer with CH$_2$Cl$_2$ (2×20 mL), wash the combined organic layer with brine, concentrate and purify the mixture with column chromatography using CH$_2$Cl$_2$ and CH$_3$OH with NH$_3$ (98:2) to give 0.22 g product.

Step 2: Dissolve the product of Step 1 (0.22 g, 0.25 mmol) in dry THF (2 mL), treat the solution with tetrabutylammonium fluoride (1M, 0.3 mL, 0.30 mmol) at 0° C. Allow the mixture to warm up to 23° C. over 30 min and stir additional 1 h. Dilute with EtOAc (50 mL) and water (50 mL), extract aqueous phase with EtOAc (2×40 mL) and concentrate the combined organic layer. Purify by column chromatography using EtOAc and hexane (1:1) to obtain 0.15 g product.

Step 3: Dissolve the product of Step 2 (140 mg, 0.32 mmol) in EtOAc (3 mL), prepare a solution of NaBr (33 mg, 0.32 mmol) in 3 mL of saturated aqueous NaHCO$_3$, and add to the reaction vessel. Add TEMPO (1 mg).

With vigorous stirring, add 1 mL of commercial bleach (ca 0.7 M, 0.7 mmol). Add saturated aqueous Na$_2$S$_2$O$_3$ (3 mL), isolate the organic layer and extract the aqueous layer with CH$_2$Cl$_2$. Combine the organic layers, wash with saturated aqueous NaHCO$_3$, and concentrate to give 140 mg aldehyde as the product.

Step 4: Hydrogenate the product of Preparation 3 using a procedure similar to that described in Example 1, Step 3. React the resulting deprotected product with the aldehyde from Step 3 in a similar procedure to that described in Example 1, Step 3, to yield the title product.

EXAMPLES 7B–7F

Prepare the compounds by a procedure similar to Example 7A using appropriate aryl acids.

EXAMPLE 8

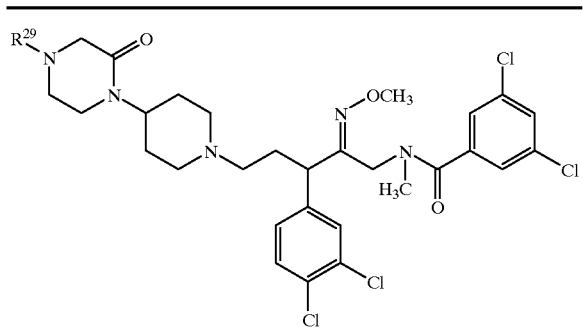

| Ex. | R²⁹ | HRMS (FAB, M + H⁺) |
|---|---|---|
| 8A | H— | Calc'd: 642.1572<br>found: 642.1555 |
| 8B | Me— | Calc'd: 656.1729<br>found: 656.1714 |
| 8C | CH₃C(O)— | Calc'd: 684.1678<br>found: 684.1660 |
| 8D | PhC(O)— | Calc'd: 746.1834<br>found: 746.1837 |
| 8E | —OC(O)CH₂C(O)— | Calc'd: 742.1733<br>found: 742.1734 |
| 8F | —NHC(O)— | LRMS 699 (M + 1) |
| 8G | —OC(O)CH₂CH₂— | Calc'd: 728.1940<br>found: 728.1934 |
| 8H | —OCH₂C(O)— | Calc'd: 714.1784<br>found: 714.1788 |
| 8I | H₂NC(O)CH₂CH₂— | Calc'd: 713.1943<br>found: 713.1944 |

-continued

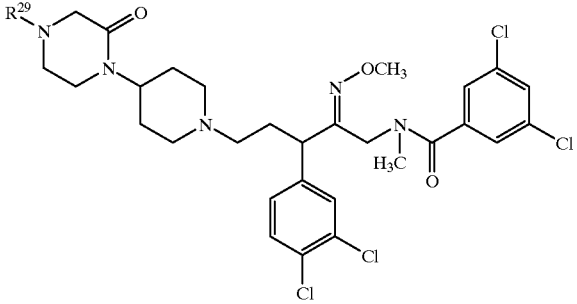

| Ex. | R²⁹ | HRMS (FAB, M + H⁺) |
|---|---|---|
| 8J | H₂NC(O)CH₂— | Calc'd: 701.1757<br>found: 701.1767 |
| 8K | CH₃CH₂S(O)₂— | Calc'd: 734.1504<br>found: 734.1523 |
| 8L | H₂NS(O)₂— | Calc'd: 721.1300<br>found: 721.1308 |

EXAMPLE 8A

Step 1: Treat the product of Preparation 8 (240 mg, 0.88 mmol) in CH₂Cl₂ (3 mL) with 2-(trimethylsilyl)ethyl 4-nitrophenyl carbonate (350 mg, 1.24 mmol), and stir for 14 h. Add water and CH₂Cl₂, and extract the aqueous layer with CH₂Cl₂ (2×20 mL), wash the combined organic layer with brine, concentrate and purify the mixture with column chromatography using CH₂Cl₂ and CH₃OH with NH₃ (98:2) to give 149 mg product.

Step 2: Treat the product of Step 1 using a procedure similar to Step 3A of Example 1. Alternatively, for optically pure product, use a procedure similar to Step 3B of Example 1.

Step 3: Treat the product of Step 2 (190 mg, 0.24 mmol) in THF (2 mL) with tetrabutylammonium fluoride (1M, 0.5 mL, 0.50 mmol), and stir for 3 h. Add water and CH₂Cl₂, and extract the aqueous layer with CH₂Cl₂ (2×20 mL), wash the combined organic layer with brine, concentrate and purify the mixture with column chromatography using CH₂Cl₂ and CH₃OH with NH₃ (95:5) to give 119 mg of the title product.

EXAMPLE 8B

Step 1: Treat the product of Preparation 8 (320 mg, 1.17 mmol) in THF (3 mL) with NaH (60% in mineral oil, 56 mg, 1.41 mmol) at 0° C. for 15 min, and add CH₃I (88 mL, 1.41 mmol). After stirring for 2 h, quench with water and CH₂Cl₂, extract the aqueous layer with CH₂Cl₂ (2×20 mL), wash the combined organic layer with brine, concentrate and purify the mixture with column chromatography using CH₂Cl₂ and CH₃OH with NH₃ (95:5) to give 180 mg product.

Step 2: Treat the product of Step 1 using a procedure similar to Step 3B of Example 1 to give the title compound.

EXAMPLE 8C

Step 1: Treat the product of Preparation 8 (250 mg, 0.92 mmol) in CH₂Cl₂ (3 mL) with ET₃N and acetyl chloride (90 mg, 1.19 mmol), and stir for 2 h. Add water and CH$_2$Cl$_2$, extract the aqueous layer with CH$_2$Cl$_2$ (2×20 mL), wash the combined organic layer with brine, concentrate and purify the mixture with column chromatography using CH$_2$Cl$_2$ and CH$_3$OH with NH$_3$ (95:5) to give 230 mg product.
Step 2: Treat the product of Step 1 using a procedure similar to Step 3 of Example 1 to give the title compound.

EXAMPLES 8D–F and 8K

Prepare the desired compounds by a procedure similar to that described in Example 8C using appropriate the acyl halide, isocyanate or sulfonyl chloride.

EXAMPLES 8G and 8H

Prepare the desired compounds by a procedure similar to that described in example 8B using appropriate alkyl halides.

EXAMPLES 8I and 8J

Prepare the target compounds by stirring a mixture of NH$_4$OH and NH$_4$Cl with the products Examples 8G and 8H in CH$_3$OH for 48 h.

EXAMPLE 8L

Treat the product of Preparation 8 (250 mg, 0.92 mmol) in 1,4-dioxane (39 mL) with sulfamide (0.6 g, 6.3 mmol), and reflux for 24 h at 80° C. Concentrate and purify the mixture with column chromatography using CH$_2$Cl$_2$ and CH$_3$OH with NH$_3$ (95:5) to give 150 mg of the title product.

EXAMPLE 9

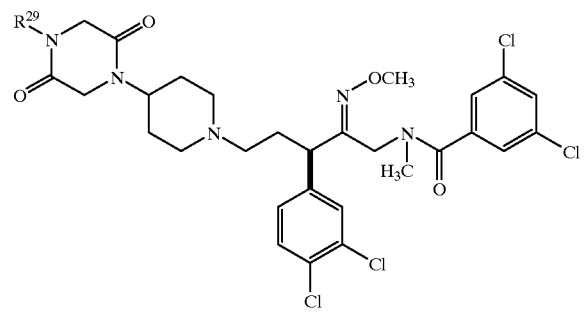

| Ex. | R$^{29}$ | HRMS (FAB, M + H$^+$) |
|---|---|---|
| 9A | H— | Calc'd: 656.1365<br>found: 656.1357 |
| 9B | Me— | Calc'd: 670.1521<br>found: 670.1514 |
| 9C | MeO–C(O)CH$_2$– | Calc'd: 728.1576<br>found: 728.1571 |

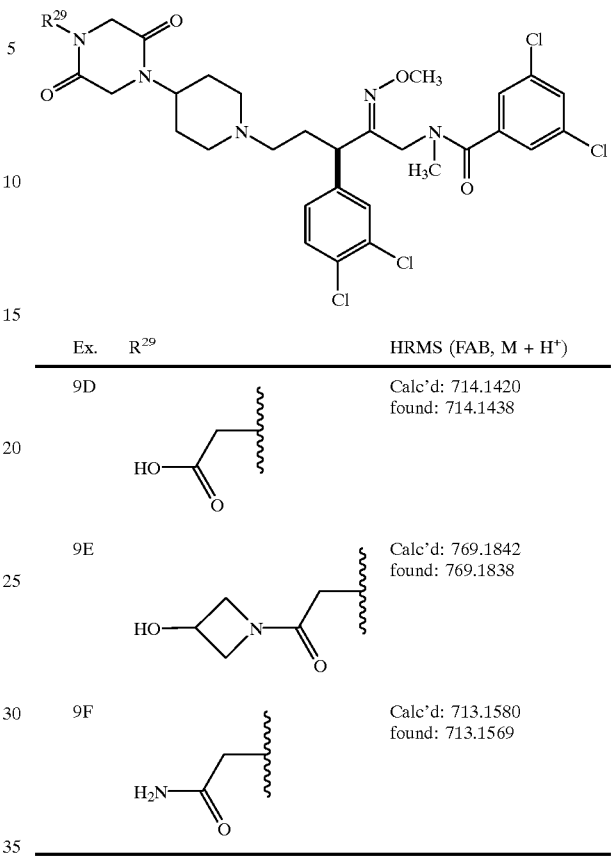

| Ex. | R$^{29}$ | HRMS (FAB, M + H$^+$) |
|---|---|---|
| 9D | HO–C(O)CH$_2$– | Calc'd: 714.1420<br>found: 714.1438 |
| 9E | HO-azetidinyl-C(O)CH$_2$– | Calc'd: 769.1842<br>found: 769.1838 |
| 9F | H$_2$N–C(O)CH$_2$– | Calc'd: 713.1580<br>found: 713.1569 |

EXAMPLE 9A

Treat the product of Preparation 9 using a procedure similar to Step 3A of Example 1. Alternatively, prepare the optically pure compound using a procedure similar to Example 1, Step 3B.

EXAMPLE 9B

Treat the product of Preparation 9 using a procedure similar to Example 8B to give the target compound.

EXAMPLE 9C

Treat the product of Preparation 9 using a procedure similar to Example 8H to give the title compound.

EXAMPLE 9D

Hydrolyze the product of Example 9C using a procedure similar to that described in Example 4A.

EXAMPLES 9E–9G

Acylate the product of Example 9D using a procedure similar to that described in Example 6G with appropriate amines.

EXAMPLE 10

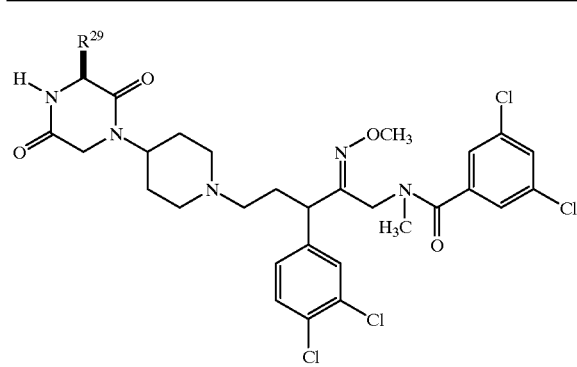

| Ex. | R²⁹ | HRMS (FAB, M + H⁺) |
|---|---|---|
| 10A | 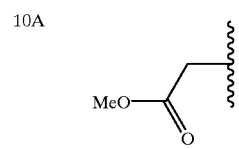 | *LRMS: 730.1 (M + 1) |
| 10B | 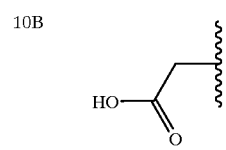 | Calc'd: 714.1420<br>found: 714.1438 |
| 10C | 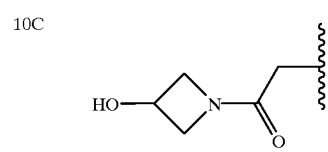 | Calc'd: 769.1842<br>found: 769.1848 |
| 10D | 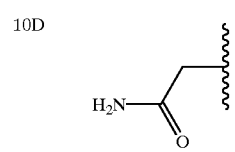 | Calc'd: 713.1580<br>found: 713.1593 |
| 10E | 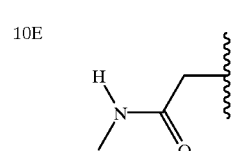 | Calc'd: 727.1736<br>found: 727.1733 |
| 10F | 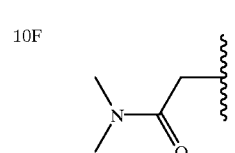 | Calc'd: 741.1893<br>found: 741.1882 |

-continued

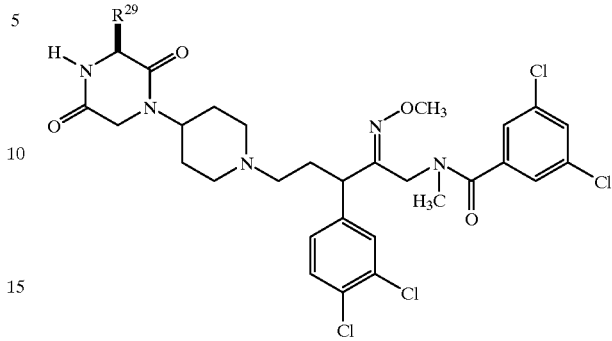

| Ex. | R²⁹ | HRMS (FAB, M + H⁺) |
|---|---|---|
| 10G | 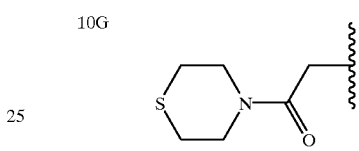 | Calc'd: 799.1770<br>found: 799.1767 |
| 10H | 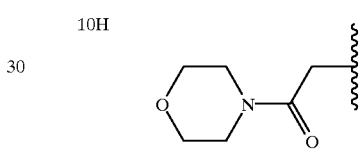 | Calc'd: 783.1998<br>found: 783.2006 |
| 10I | 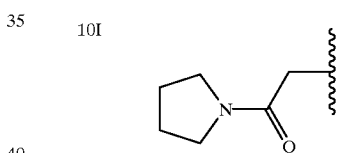 | Calc'd: 767.2049<br>found: 767.2054 |

EXAMPLE 10A

Prepare title compound by a procedure similar to Preparation 9 using L-N-Boc-aspartic acid methyl ester in place of glycine methyl ester.

EXAMPLES 10B–10I

Prepare the desired compounds by standard hydrolysis and acylation procedures similar to those described in Examples 9D–9G.

EXAMPLE 11

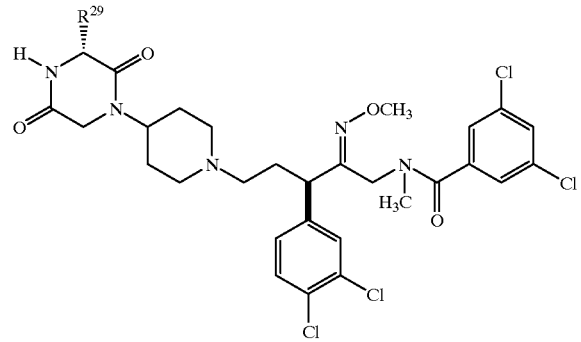

| Ex. | R²⁹ | HRMS (FAB, M + H⁺) |
|---|---|---|
| 11A | 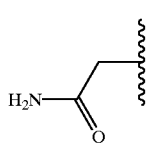 | Calc'd: 713.1580<br>found: 713.1593 |
| 11B | 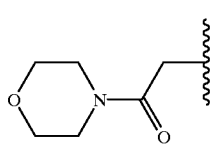 | Calc'd: 783.1998<br>found: 783.2012 |
| 11C | 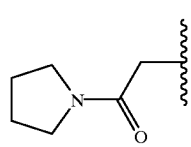 | Calc'd: 767.2049<br>found: 767.2061 |
| 11D | 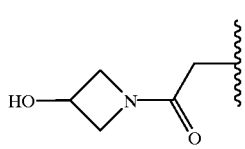 | Calc'd: 769.1842<br>found: 769.1817 |

EXAMPLES 11A–11D

Prepare the desired compounds by procedures similar to Example 10, using D-N-Boc-aspartic acid benzyl ester in place of L-N-Boc-aspartic acid methyl ester.

EXAMPLE 12

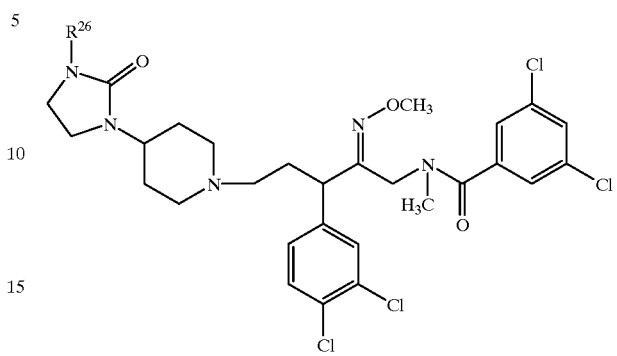

| Ex. | R²⁶ | HRMS (FAB, M + H⁺) |
|---|---|---|
| 12A |  | Calc'd: 628.1416<br>found: 628.1434 |
| 12B | 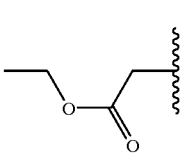 | Calc'd: 714.1784<br>found: 714.1765 |
| 12C | 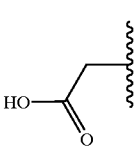 | Calc'd: 686.1471<br>found: 686.1482 |
| 12D | 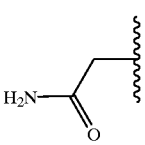 | Calc'd: 687.1601<br>found: 687.1603 |
| 12E | 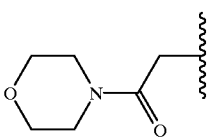 | Calc'd: 755.2049<br>found: 755.2047 |
| 12F | 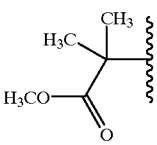 | Calc'd: 714.1784<br>found: 714.1776 |
| 12G | 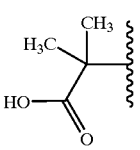 | Calc'd: 728.1940<br>found: 728.1945 |

-continued

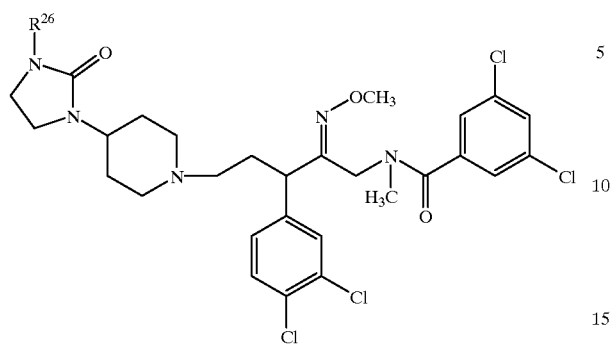

| Ex. | $R^{26}$ | HRMS (FAB, M + H$^+$) |
|---|---|---|
| 12H | H$_3$C—C(CH$_3$)(NH$_2$)—C(O)— | Calc'd: 713.1943<br>found: 713.1945 |
| 12I | H$_3$C— | Calc'd: 642.1572<br>found: 642.1562 |

EXAMPLE 12A

Step 1: Dissolve the product of Preparation 8, Step 1 (2.7 g, 8.1 mmol) in CH$_2$Cl$_2$ (40 mL), treat with 4 M HCl in dioxane (40 mL, 160 mmol) and stir for 2 h. Remove solvent under reduced pressure to yield a crude product. Re-dissolve the product in THF (45 mL), treat with carbonyldiimidazole (2.26 g, 13.9 mmol) and reflux for 24 h. Remove solvent under reduced pressure and dilute with CH$_2$Cl$_2$ and NaHCO$_3$. Separate the organic layer, concentrate and purify the mixture with column chromatography using CH$_2$CO$_2$ and CH$_3$OH with NH$_3$ (96:4) to give 1.8 g product.
Step 2: Treat the product of Step 1 by a procedure similar to Example 1, Step 3 to give the product.

EXAMPLE 12B

Step 1: Use a procedure described in Preparation 11, substituting 2-amino-ethanol for 3-amino-1-propanol to obtain the product.
Step 2: Treat the product of Step 1 by a procedure similar to Preparation 12A using glycine ethyl ester in place of methylamine.
Step 3: Treat the product of Step 2 by a procedure similar to Example 1,
Step 3, using acid deprotection (HCl in CH$_2$Cl$_2$) in place of hydrogenation.

EXAMPLE 12C

Hydrolyze the product of Example 12B in a manner similar to Example 4A to give the desired product.

EXAMPLES 12D and 9E

Treat the product of Example 12C by an amidation procedure similar to that described in Example 4E to give the title product.

EXAMPLE 12F

Step 1: Use the procedure of Preparation 11, substituting 2-aminoethanol for 3-amino-1-propanol.
Step 2: Treat the product of Step 1 using a procedure similar to Example 6L, Steps 2–4, to obtain the title compound.

EXAMPLES 12G–12H

Treat the product of Example 12F using a procedure similar to Examples 6M and 6N to obtain the title compounds.

EXAMPLE 12I

Treat the product of Example 12F, Step 1, using a procedure similar to Example 6P to obtain the title compound.

EXAMPLE 13

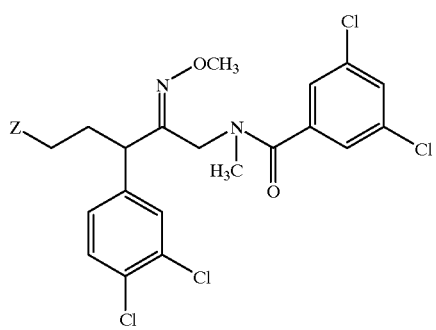

| Ex. | Z | MS |
|---|---|---|
| 13A | 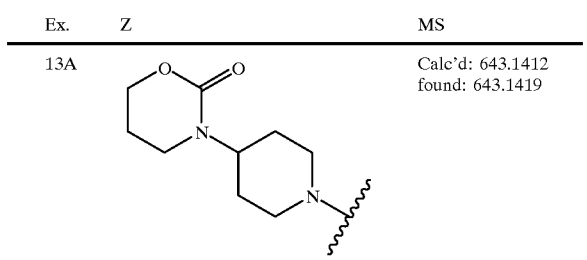 | Calc'd: 643.1412<br>found: 643.1419 |
| 13B | 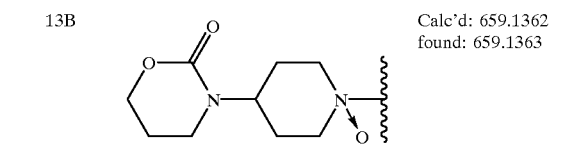 | Calc'd: 659.1362<br>found: 659.1363 |

EXAMPLE 13A

Treat the product of Preparation 10 using a procedure similar to Example 1, Step 3 to yield the title compound.

EXAMPLE 13B

Treat the product of Example 13A using a procedure similar to that described in Preparation 12I–12L to yield the title compound.

EXAMPLE 14

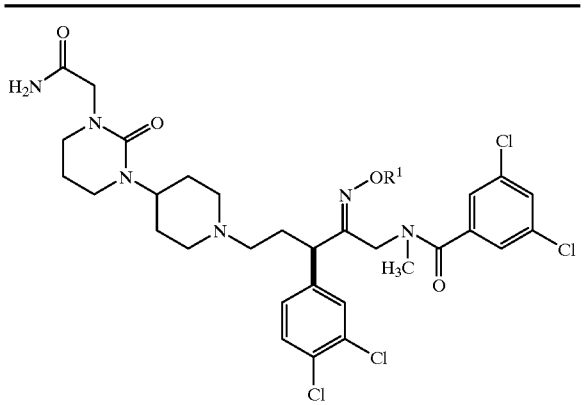

| Ex. | R1 | MS (FAB): m/e |
|---|---|---|
| 14A | (=N-OH, NH2) | Calc'd: 757.1954<br>found: 757.1945 |
| 14B | (=N-OMe, NH2) | Calc'd: 771.2111<br>found: 771.2099 |
| 14C | (=N-OH with -O-CH2-C(=NH)-NH2 linker, NH2) | Calc'd: 829.2278<br>found: 829.2269 |

EXAMPLE 14A

Step 1: Treat 3,5-dichloro-N-[3-(3,4-dichlorophenyl)-2-[[hydroxyimino]-6-methyl-5-heptenyl]-N-methylbenzamide (4.2 g, 8.6 mmol) in dry DMF(40 mL) at 0° C. with KHMDS (0.5 M, toluene, 19 mL) keeping the internal temperature to <5° C. After stirring for 30 min, add bromoacetonitrile (655 μL, 9.4 mmol) and stir for 10 min. Pour the mixture into EtOAc (150 mL)/sat NaHCO₃ (75 mL). Extract the aqueous layer, wash the combined organic layers with brine, dry with Na₂SO₄ and concentrate in vacuo. Purify by silica gel chromatography eluting with hexane/EtOAc to obtain 3.83 g (85%) of the nitrile as a colorless foam.

Step 2: Cool a solution of the olefin (3.83 g) from step 1 (in dry CH₂Cl₂ (50 mL) to −78° C. and treat with ozone for 7 min. Treat the solution with dimethylsulfide (5.3 mL, 72.6 mmol, 10 eq). Allow the solution to warm to 23° C. and stir for 2.5 h. Dilute the solution with CH₂Cl₂ (50 mL) and wash with 10% Na₂S₂O₄. Wash the organic layers with brine, dry with Na₂SO₄ and concentrate in vacuo to give the aldehyde.

Step 3: Treat the product of step 2 using a procedure similar to Example 6FF.

Step 4: Treat the product of step 3 using a procedure similar to that of Example 6GG to obtain the corresponding hydroxyamidine.

EXAMPLE 14B

Treat Example 14A using a procedure similar to that of Example 14A, step 1, using LHMDS in place of KHMDS and CH₃I as the alkylating agent to obtain the title compound.

EXAMPLE 14C

Treat the product of Example 14A using a procedure similar to that of Example 14A, step 1, and then step 4 to give the desired compound.

| Ex. | R¹ | HRMS (FAB): m/e |
|---|---|---|
| 15A | (=N-OH, NH2) | Calc'd: 700.1739<br>found: 771.2099 |
| 15B | (=O, NH2) | Calc'd: 685.1630<br>found: 685.1627 |

EXAMPLE 15A

Use a procedure similar to that of Example 14A using the product of example 6O, step 1 as the piperidine in the reductive amination for step 3. Proceed to step 4 to give the title compound.

EXAMPLE 15B

Use a procedure similar to that for Example 6A using methylbromoacetate in place of bromoacetonitrile. Proceed through the reductive amination with the product of Example 6O, step 1 to give the methyl ester. Stir the resulting methyl ester with CH₃OH saturated with NH₃ for 18 h. Concentrate in vacuo and purify by silica gel chromatography to give the title compound.

EXAMPLE 16

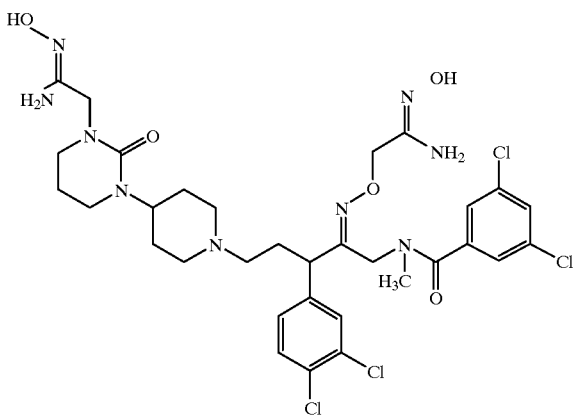

Treat the product of Example 14A, step 3 to a procedure similar to that of Example 6GG to give the title compound. HRMS (FAB, m/e): Calc'd: 772.2063; found: 772.2059.

EXAMPLE 17

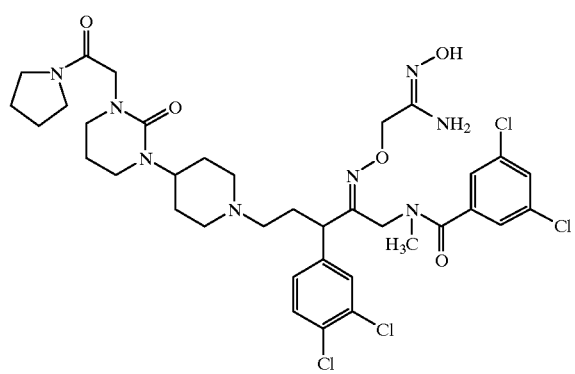

Step 1: Using a procedure similar to Preparation 12C–12H and substituting glycine methylester for the appropriate amine, prepare the corresponding cyclic urea/Boc piperidine.

Step 2: Using a procedure similar to Example 4A, hydrolyze the methyl ester to the carboxylic acid.

Step 3: Using a procedure similar to Example 4B to prepare the corresponding pyrrolidine amide.

Step 4: Using a procedure similar to Preparation 12A, step 3, deprotect the Boc group and isolate the free base of the resulting piperdine.

Step 5: Use the product of step 4 in a procedure similar to Example 14A, steps 3 and 4 to prepare the title compound. HRMS (FAB, M+H$^+$): Calc'd: 811.2424; found: 811.2441.

EXAMPLE 18

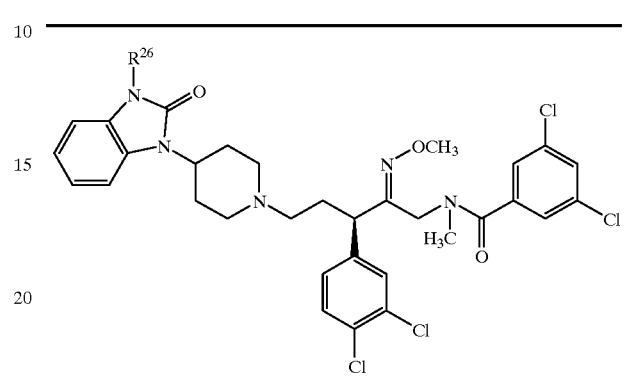

| Ex. | R$^{26}$ | HRMS (FAB, M + H$^+$) |
|---|---|---|
| 18A | H | Calc'd: 676.1416 |
|  |  | Found: 676.1389 |
| 18B | CH$_3$— | Calc'd: 692.1543 |
|  |  | Found: 692.1558 |
| 18C | H$_3$CO-CH$_2$-C(=O)- | Calc'd: 748.1627 |
|  |  | Found: 748.1621 |
| 18D | HO-CH$_2$-C(=O)- | Calc'd: 734.1471 |
|  |  | Found: 734.1487 |

EXAMPLE 18A

Treat 4-(2-keto-1-benzimidazolinyl)-piperidine and the product of Preparation 2 using the procedure of Example 2, Step 2, to give the title compound.

EXAMPLES 18B–18D

Treat the product of Example 18A using the procedure in Examples 9B, 9C and 9D to give the title compounds.

EXAMPLE 19

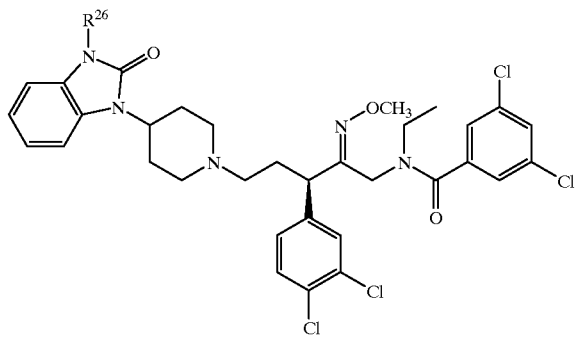

| Ex. | R²⁶ | HRMS (FAB, M + H⁺) |
|---|---|---|
| 19A | CH₃O(CH₂)₂— | Calc'd: 772.1852 |
| | | Found: 772.1859 |
| 19B | CH₃O(CH₂)₂NHC(O)CH₂— | Calc'd: 805.2206 |
| | | Found: 805.2195 |

EXAMPLE 19A

Step 1: Treat Boc-4-(2-keto-1-benzimidazolinyl)-piperidine (3.0 g, 9.46 mmol) with a preheated mixture of NaOH (1.14 g, 28.2 mmol), K₂CO₃ (2.61 g, 18.9 mmol) and nBuNHSO₄ (0.305 g, 0.9 mmol) in toluene (75 ml) for 30 min., add 2-bromomethoxyethane (1.33 ml, 14.2 mmol) and heat at 80° C. for an additional hour. Upon cooling, treat the mixture with water and EtOAc, adjust pH to 7 using 10% citric acid. Extract with EtOAc, dry the organic layer with Na₂SO₄ and concentrate in vacuo to give a crude product. Step 2: Deprotect the Boc group of the product of Step 1 using a similar procedure as in Preparation 12A, Step 3. Treat the product using a procedure similar to Example 1, Step 3B, using the corresponding optically pure aldehyde (prepared as in Preparation 1) to give the desired product.

EXAMPLE 19B

Use a procedure similar to that of Example 18C using the corresponding aldehyde (prepared as in Preparation 1) to give a product. Dissolve the product (0.5 g, 0.655 mmol) in 2-methoxyethylamine (10 ml), and heat at 60° C. for 24 h. Upon cooling, treat the mixture with water and EtOAc. Extract with EtOAc, dry the organic layer with Na₂SO₄ and concentrate in vacuo to give a crude product. Purify by silica gel chromatography, eluting with CH₂Cl₂/CH₃OH gradient elution (99:1–97:3) to obtain 0.277 g of the desired product.

Compounds of formula I have been found to be antagonists of NK₁ and/or NK₂ and/or NK₃ receptors, and are therefore useful in treating conditions caused or aggravated by the activity of said receptors.

The in vitro and in vivo activity of the compounds of formula I can be determined by various procedures known in the art, such as a test for their ability to inhibit the activity of the NK₁ agonist Substance P, an isolated hamster trachea NK₂ assay, a test of the effect of NK₁ antagonists on Substance P-induced airway microvascular leakage, measurement of NK₂ activity in vivo in guinea pigs, measurement of bronchoconstriction due to NKA, and neurokinin receptor binding assay(s). NK₃ activity is determined by following a procedure similar to that described in the literature, e.g., *Molecular Pharmacol.*, 48 (1995), p. 711–716. Typical procedures for determining NK₁ and NK₂ activity are described in U.S. Pat. No. 5,696,267, incorporated herein by reference.

% Inhibition of neurokinin agonist activity is the difference between the percent of maximum specific binding (MSB) and 100%. The percent of MSB is defined by the following equation, wherein "dpm" is disintegrations per minute:

$$\% \ MSB = \frac{(dpm \ \text{of unknown}) - (dpm \ \text{of nonspecific binding})}{(dpm \ \text{of total binding}) - (dpm \ \text{of nonspecific binding})} \times 100$$

It will be recognized that compounds of formula I exhibit NK₁, NK₂ and/or NK₃ antagonist activity to varying degrees, e.g., certain compounds have strong NK₁ antagonist activity, but weaker NK₂ and NK₃ antagonist activity, while others are strong NK₂ antagonists, but weaker NK₁ and NK₃ antagonists. While compounds with approximate equipotency are preferred, it is also within the scope of this invention to use compounds of with unequal NK₁/NK₂/NK₃ antagonist activity when clinically appropriate.

Using the test procedures known in the art, the following data (% inhibition or Ki) were obtained for preferred and/or representative compounds of formula I:

| Ex. | Ki (NK₁) (nM) | Ki (NK₂) (nM) | Ki (NK₃) (nM) |
|---|---|---|---|
| 5B | 0.9 | 2.8 | — |
| 6E | 1.0 | 1.0 | 1.5 |
| 6K | 0.5 | 0.8 | 0.5 |
| 6Y | 0.4 | 0.4 | 0.4 |
| 8A | 1.1 | 0.7 | 1.2 |
| 10B | 2.9 | 28.9 | 34.6 |
| 11A | 0.8 | 1.0 | 1.9 |
| 7F | 1.8 | 0.4 | 3.8 |
| 16 | 0.4 | 0.4 | 0.7 |
| 18A | 1.2 | 1.0 | 9.8 |
| 6M | 0.9 | 0.5 | 0.3 |
| 6S | 1.0 | 0.9 | 2.1 |

Compounds of the present invention exhibit a range of activity: percent inhibition at a dosage of 1 μM ranges from about 0 to about 100% inhibition of NK₁ and/or about 0 to about 100% inhibition of NK₂. Preferred are compounds having a Ki≦20 nM for the NK₁ receptor. Also preferred are compounds having a Ki≦20 nM for the NK₂ receptor. Another group of preferred compounds are those having a Ki≦20 nM for each of the NK₁ and NK₂ receptors.

We claim:

1. A compound represented by the structural formula

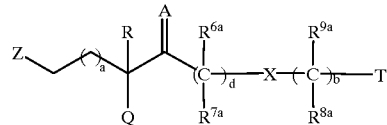

or a pharmaceutically acceptable salt thereof, wherein:
  a is 0, 1, 2 or 3;
  b and d are independently 0, 1 or 2;
  R is H, C₁₋₆ alkyl, —OR⁶ or —F;
  A is =N—OR¹;
  when d is not 0, X is a bond, —C(O)—, —O—, —NR⁹—, —S(O)ₑ—, —N(R⁶)C(O)—, —C(O)N(R⁶)—, —OC(O)NR⁶—, —OC(=S)NR⁶—, —N(R⁶)C(=S)O—, —S(O)₂N(R⁶)—, —N(R⁶)S(O)₂—, —N(R⁶)C(O)O—, —OC(O)— or —N(R⁶)C(O)NR⁷—; and
when d is 0, X is a bond or —NR⁶—;

T is H, R⁴-aryl or R⁴-heteroaryl;

Q is R⁵-phenyl, or R⁵-naphthyl;

R¹ is H, C₁₋₆ alkyl, —(C(R⁶)(R⁷))ₙ—G, —G², or —(C(R⁶)(R⁷))ₚ—M—(C(R¹³)(R¹⁴))ₙ—G;

R⁴ and R⁵ are independently 1–3 substituents independently selected from the group consisting of H, halogeno, —OR⁶, —OC(O)R⁶, —OC(O)N(R⁶)(R⁷), —N(R⁶)(R⁷), C₁₋₆ alkyl, —CF₃, —C₂F₅, —COR⁶, —CO₂R⁶, —CON(R⁶)(R⁷), —S(O)ₑR¹³, —CN, —OCF₃, —OCHF₂, —NR⁶CO₂R¹⁶, —NR⁶COR⁷, —NR⁸CON(R⁶)(R⁷), NO₂, —N(R⁶)S(O)₂R¹³ or —S(O)₂N(R⁶)(R⁷); or adjacent R⁴ substituents or adjacent R⁵ substituents can form a —O—CH₂—O— group;

R⁶, R⁷, R⁸, R¹³ and R¹⁴ are independently selected from the group consisting of H, C₁₋₆ alkyl, C₂–C₆ hydroxyalkyl, C₁–C₆ alkoxy-C₁–C₆ alkyl, R¹⁵-phenyl, and R¹⁵-benzyl;

R⁹ is independently selected from the group consisting of R⁶ and —OR⁶;

or R⁶ and R⁷, or R⁷ and R⁹, together with the nitrogen to which they are attached, form a ring of 5 to 6 members, wherein 0, 1 or 2 ring members are selected from the group consisting of —O—, —S— and —N(R¹⁹)—;

R⁶ᵃ, R⁷ᵃ, R⁸ᵃ, R⁹ᵃ, R¹⁰ and R¹⁰ᵃ are independently selected from the group consisting of H and C₁₋₆ alkyl;

R¹⁵ is 1 to 3 substituents independently selected from the group consisting of H, —OH, C₁–C₆ alkyl, C₁–C₆ alkoxy, C₁–C₆ alkylthio, halogeno, —CF₃, —C₂F₅, —COR¹⁰, —CO₂R¹⁰, —C(O)N(R¹⁰)₂, —S(O)ₑR¹⁰ᵃ —CN, —N(R¹⁰)COR¹⁰, —N(R¹⁰)CON(R¹⁰)₂ and —NO₂;

R¹⁶ is C₁₋₆ alkyl, R¹⁵-phenyl or R¹⁵-benzyl;

R¹⁹ is H, C₁–C₆ alkyl, —C(O)N(R¹⁰)₂ or —CO₂R¹⁰;

n and p are independently 1–6;

G is selected from the group consisting of H, R⁴-aryl, R⁴-heterocycloalkyl, R⁴-heteroaryl, R⁴-cycloalkyl, —CH₂F, —CHF₂, —CF₃, —OR⁶, —N(R⁶)(R⁷), —COR⁶, —CO₂R⁶, —CON(R⁷)(R⁹), —S(O)ₑR¹³, —NR⁶CO₂R¹⁶, —NR⁶COR⁷, —NR⁸CON(R⁶)(R⁷), —N(R⁶)S(O)₂R¹³, —N(R⁶)S(O)₂N(R³³)(R³⁴), —S(O)₂N(R⁶)(R⁷), —C(O)R⁶, —OC(O)N(R⁶)(R⁷), —C(=NOR⁸)N(R⁶)(R⁷), —C(=NR²⁵)N(R⁶)(R⁷), —N(R⁸)C(=NR²⁵)N(R⁶)(R⁷), —CN, —C(O)N(R⁶)OR⁷, and —C(O)N(R⁹)-(R⁴-heteroaryl), provided that when n is 1, G is not —OH or —N(R⁶)(R⁷);

M is selected from the group consisting of a double bond, —O—, —N(R⁶)—, —C(O)—, —C(R⁶)(0R⁷)—, —C(R⁸)(N(R⁶)(R⁷))—, —C(=NOR⁶)N(R⁷)—, —C(N(R⁶)(R⁷))=NO—, —C(=NR²⁵)N(R⁶)—, —C(O)N(R⁹)—, —N(R⁹)C(O)—, —C(=S)N(R⁹)—, —N(R⁹)C(=S)— and —N(R⁶)C(O)N(R⁷)—, provided that when n is 1, G is not OH or —NH(R⁶); and when p is 2–6, M can also be —N(R⁶)C(=NR²⁵)N(R⁷)— or —OC(O)N(R⁶)—;

G² is R⁴-aryl, R⁴-heterocycloalkyl, R⁴-heteroaryl, R⁴-cycloalkyl, —COR⁶, —CO₂R¹⁶, —S(O)₂N(R⁶)(R⁷) or —CON(R⁶)(R⁷);

e is 0, 1 or 2, provided that when e is 1 or 2, R¹³ and R¹⁰ᵃ are not H;

R²⁵ is H, C₁–C₆ alkyl, —CN, R¹⁵-phenyl or R¹⁵-benzyl;

Z is

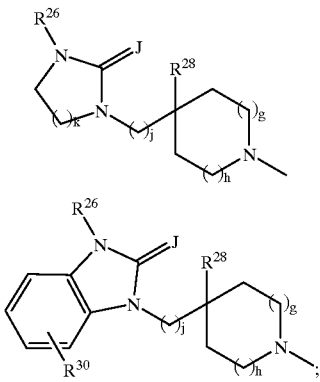

g, h and j are independently 0–2;

k is 1–4;

J is =O, =S, =NR⁹, =NCN or =NOR¹;

R²⁶, is H, C₁₋₆ alkyl, —(C(R⁶)(R⁷))ₙ—G, —G², —C(O)—(C(R⁸)(R⁹))ₙ—G, OH, —OC(O)NH₂ or —S(O)ₑR¹³;

R²⁸ is H, —(C(R⁶)(R⁷))ₜ—G or —CON(R⁶)(R⁷);

t is 0, 1, 2 or 3, provided that when j is 0, t is 1, 2 or 3;

R³⁰ is 1–3 substituents independently selected from the group consisting of H, halogeno, —OR⁶, —OC(O)R⁶, —OC(O)N(R⁶)(R⁷), —N(R⁶)(R⁷), C₁₋₆ alkyl, —CF₃, —C₂F₅, —COR⁶, —CO₂R⁶, —CON(R⁶)(R⁷), —S(O)ₑR¹³, —CN, —OCF₃, —NR⁶CO₂R¹⁶, —NR⁶COR⁷, —NR⁸CON(R⁶)(R⁷), NO₂, —N(R⁶)S(O)₂R¹³ or —S(O)₂N(R⁶)(R⁷); or adjacent R³⁰ substituents can form a —O—CH₂—O— group; and R³³ and R³⁴ are independently selected from the group consisting of H, C₁–C₆ alkyl, R¹⁵-phenyl and R¹⁵-benzyl;

wherein heterocycloalkyl is a 4- to 6-membered saturated ring comprising 1 to 3 heteroatoms independently selected from the group consisting of —O—, —S— and —N(R¹⁹)—, with the remaining ring members being carbon, and heteroaryl is a 5- to 10 membered single or benzofused aromatic ring comprising 1 to 4 heteroatoms independently selected from —O—, —S— and —N=, provided that the rings do not include adjacent oxygen or sulfur atoms.

2. A compound of claim 1 wherein d is not 0 and X is —O—, —C(O)—, a bond, —NR⁹—, —S(O)ₑ—, —N(R⁶)C(O)—, —C(O)NR⁶ or —OC(O)NR⁶—.

3. A compound of claim 1 wherein T is R⁴-aryl or R⁴-heteroaryl.

4. A compound of claim 1 wherein Q is R⁵-phenyl.

5. A compound of claim 1 wherein Z is

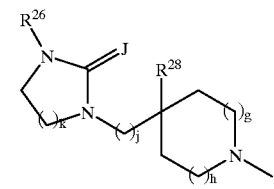

-continued

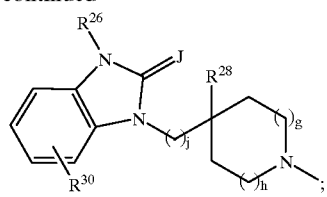

g and h are each 1; J is =O; j is 0; k is 1 or 2; and R²⁸ is H.

6. A compound of claim 1 wherein d is not 0 and X is —O—, —C(O)—, a bond, —NR⁹—, —S(O)$_e$—, —N(R⁶)C(O)—, —C(O)NR⁶ or —OC(O)NR⁶—; T is R⁴-aryl or R⁴-heteroaryl; Q is R⁵-phenyl; Z is

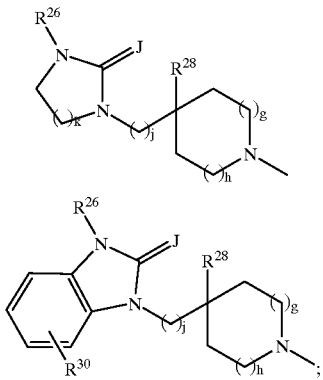

g and h are each 1; J is=O; j is 0; k is 1 or 2; and R²⁸ is H.

7. A compound of claim 6 wherein A is =N—OR¹, X is —N(R⁶)C(O)—, T is R⁴-aryl; Q is R⁵-phenyl; and R⁶ᵃ, R⁷ᵃ, R⁸ᵃ and R⁹ᵃ are each H.

8. A compound of claim 7 wherein Z is

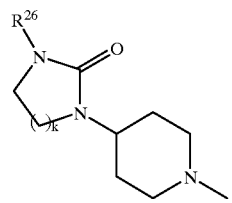

and k is 1 or 2.

9. A pharmaceutical composition comprising an effective amount of a compound of claim 1 and a pharmaceutically acceptable carrier.

10. A compound selected from the group of compounds represented by the formula

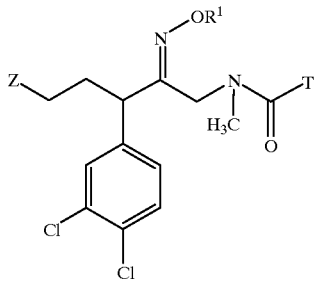

wherein Z, R¹ and T are as defined in the table:

| Z | R¹ | T |
|---|----|----|
| ![structure] | —CH₃ | ![3,5-dichlorophenyl] |
| ![structure] | —CH₃ | ![3,5-dichlorophenyl] |
| ![structure] | —CH₂C(O)NH₂ | ![3,5-dichlorophenyl] |

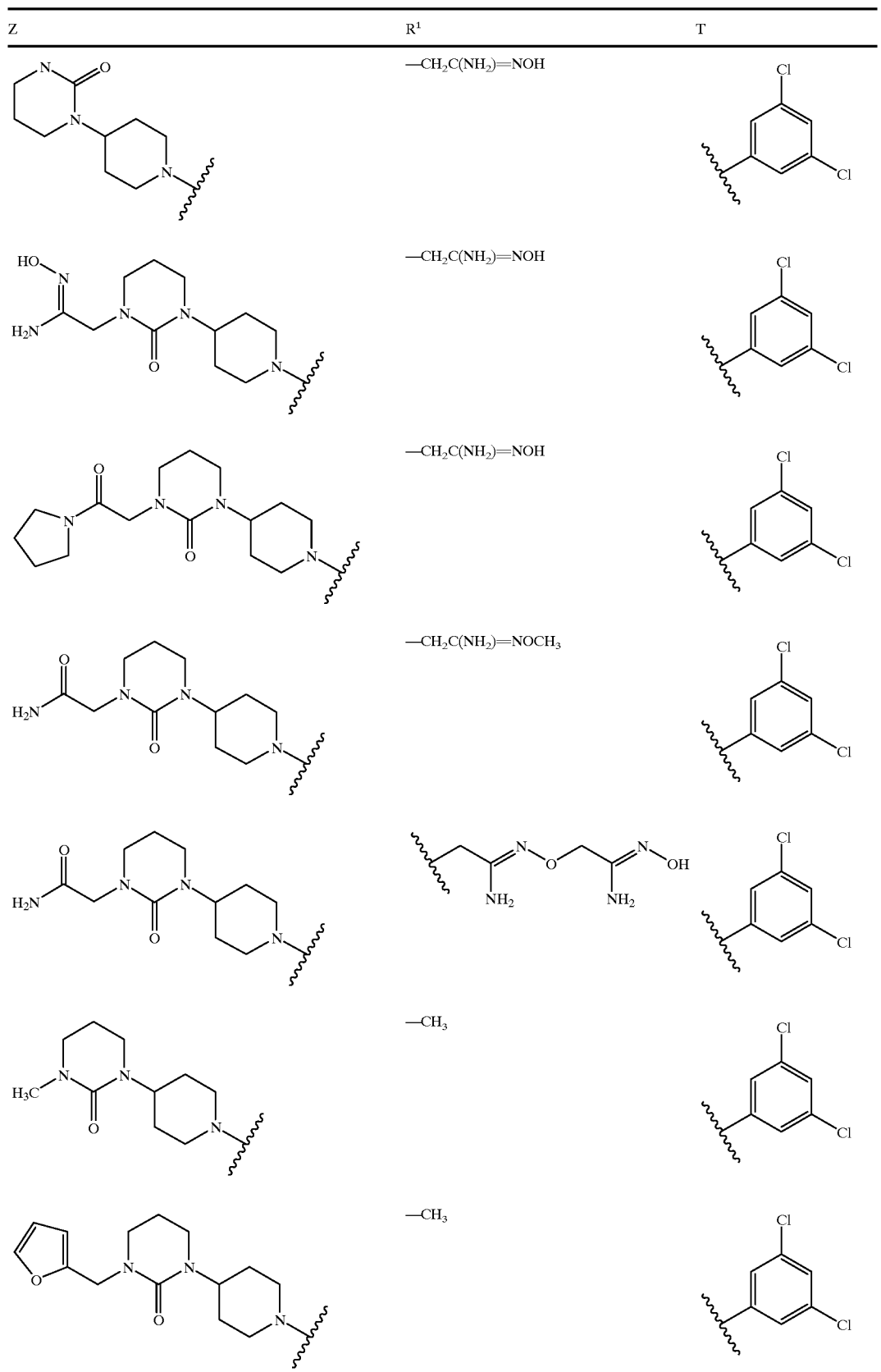

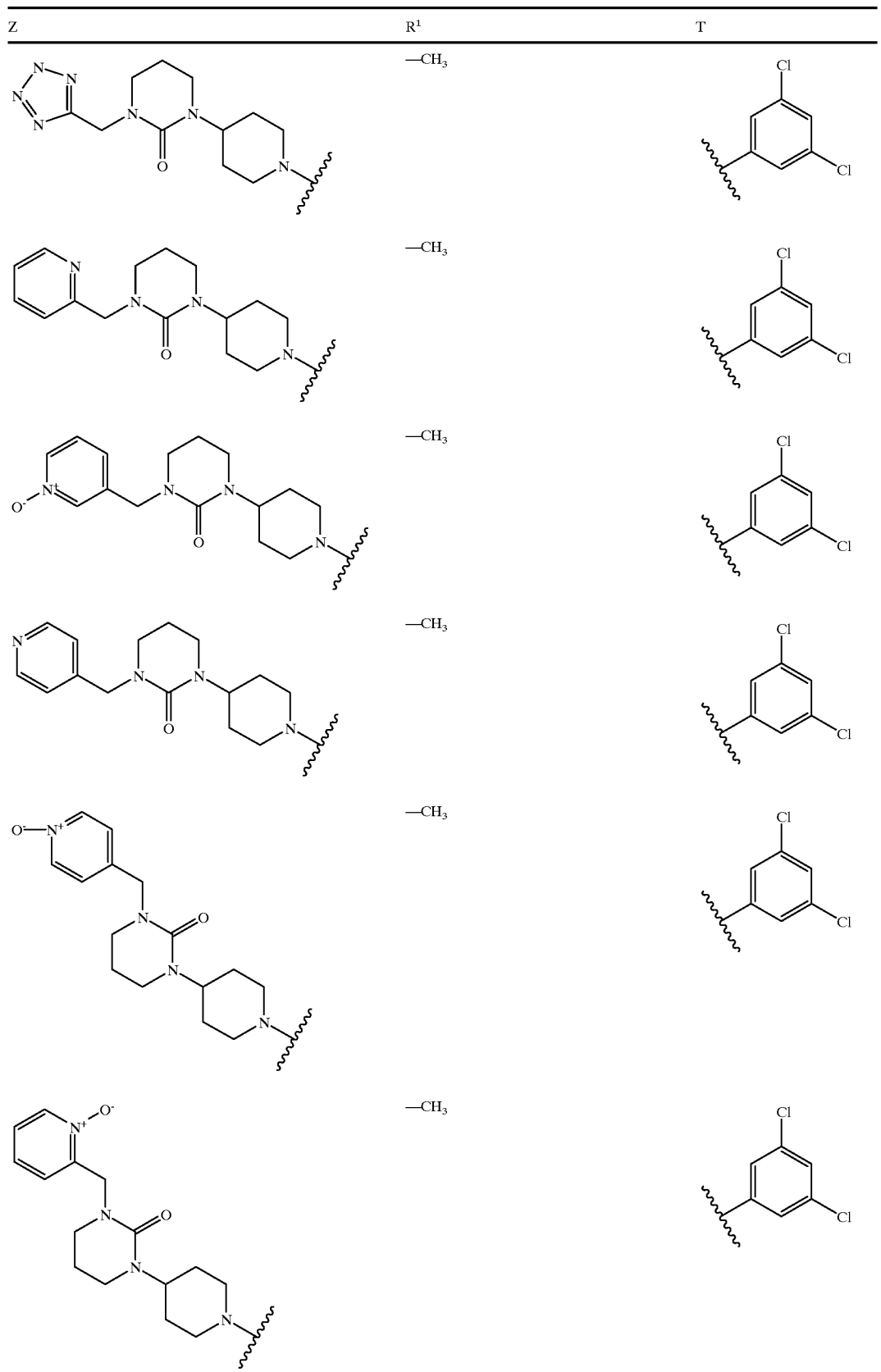

-continued
| Z | R¹ | T |
|---|---|---|
| 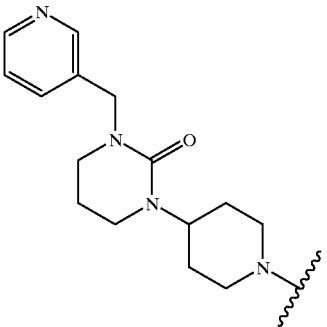 | —CH₃ | 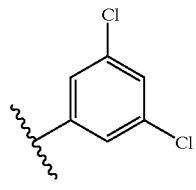 |
| 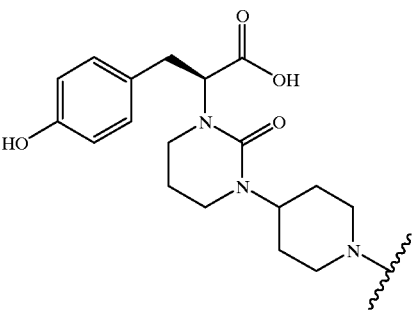 | —CH₃ | 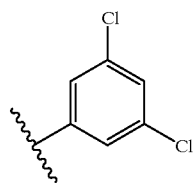 |
| 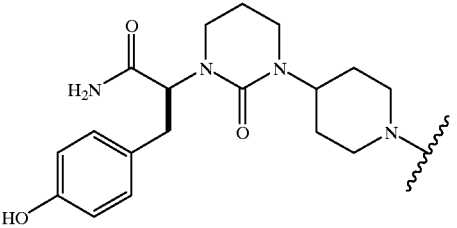 | —CH₃ | 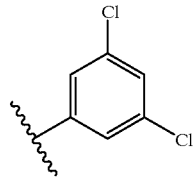 |
| 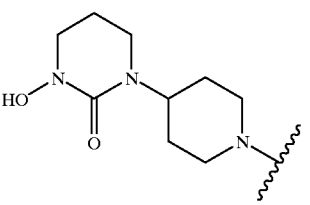 | —CH₃ | 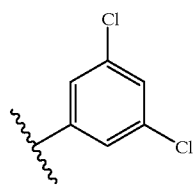 |
| 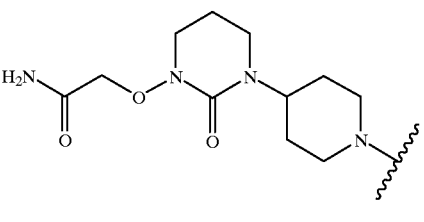 | —CH₃ | 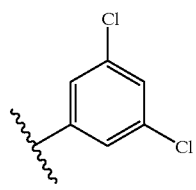 |
| 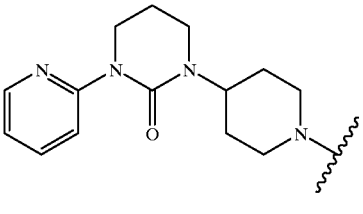 | —CH₃ | 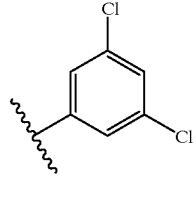 |

-continued

| Z | R¹ | T |
|---|----|---|
| [pyridine N-oxide-tetrahydropyrimidinone-piperidine] | —CH₃ | 3,5-dichlorophenyl |
| [amidinomethyl-tetrahydropyrimidinone-piperidine] | —CH₃ | 3,5-dichlorophenyl |
| [morpholinocarbonylmethyl-tetrahydropyrimidinone-piperidine] | —CH₃ | 3,5-dichlorophenyl |
| [tetrahydropyrimidinone-piperidine] | —CH₃ | 3-CF₃-phenyl |
| [tetrahydropyrimidinone-piperidine] | —CH₃ | 3,4-methylenedioxyphenyl |
| [2-hydroxyethyl-tetrahydropyrimidinone-piperidine] | —CH₃ | 3,5-dichlorophenyl |
| [2-hydroxy-2-methylpropyl-tetrahydropyrimidinone-piperidine] | —CH₃ | 3,5-dichlorophenyl |

-continued

| Z | R¹ | T |
|---|----|---|
| ethyl (2-oxo-3-(piperidin-4-yl)tetrahydropyrimidin-1-yl)acetate group | —CH₃ | 3,5-dichlorophenyl |
| 3-(2-oxo-3-(piperidin-4-yl)tetrahydropyrimidin-1-yl)propanoic acid group | —CH₃ | 3,5-dichlorophenyl |
| 2-(2-oxo-3-(piperidin-4-yl)imidazolidin-1-yl)acetamide group | —CH₃ | 3,5-dichlorophenyl |
| 1-(piperidin-4-yl)imidazolidin-2-one group | —CH₂C(NH₂)=NOH | 3,5-dichlorophenyl |
| 2-methyl-2-(2-oxo-3-(piperidin-4-yl)tetrahydropyrimidin-1-yl)propanoic acid group | —CH₃ | 3,5-dimethylphenyl |
| 2-methyl-2-(2-oxo-3-(piperidin-4-yl)tetrahydropyrimidin-1-yl)propanamide group | —CH₃ | 3,5-dichlorophenyl |
| methyl 2-methyl-2-(2-oxo-3-(piperidin-4-yl)tetrahydropyrimidin-1-yl)propanoate group | —CH₃ | 3,5-dichlorophenyl |

| Z | R¹ | T |
|---|---|---|
| 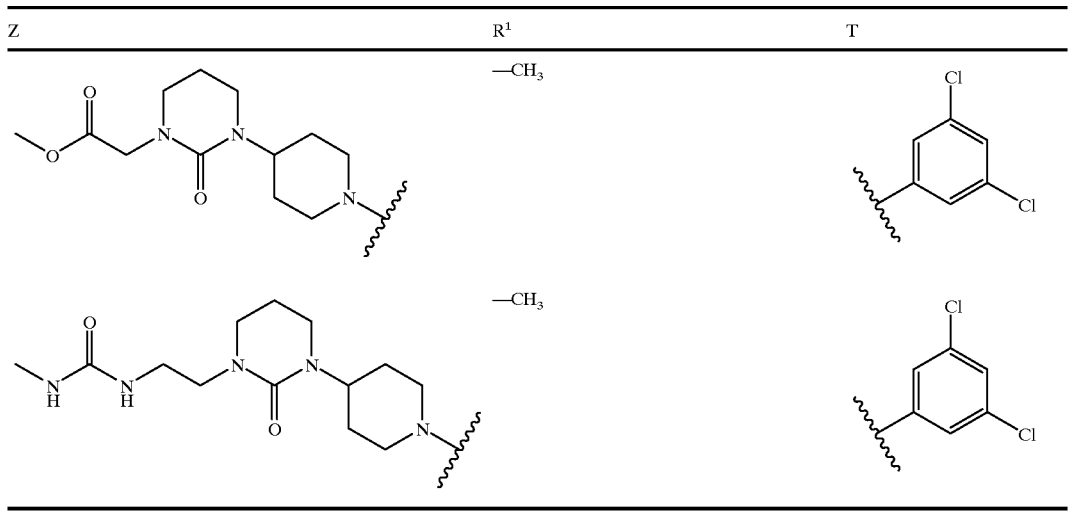 | —CH₃ —CH₃ | |

11. A method for treating asthma, bronchospasm, allergies, anxiety, depression, coughing or pain, comprising administering a therapeutically effective amount of a compound according to claim 1 to a mammal in need of such treatment.

12. A compound of claim 1 represented by the structural formula

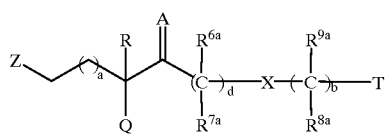

or a pharmaceutically acceptable salt thereof, wherein:

a is 0, 1, 2 or 3;

b and d are independently 0, 1 or 2;

R is H, $C_{1-6}$ alkyl, —$OR^6$ or —F;

A is =N—$OR^1$;

when d is not 0, X is a bond, —C(O)—, —O—, —$NR^9$—, —S(O)$_e$—, —N($R^6$)C(O)—, —C(O)N($R^6$)—, —OC(O)$NR^6$—, —OC(=S)$NR^6$—, —N($R^6$)C(=S)O—, —S(O)$_2$N($R^6$)—, —N($R^6$)S(O)$_2$—, —N($R^6$)C(O)O—, —OC(O)— or —N($R^9$)C(O)$NR^7$—; and when d is 0, X is a bond or —$NR^6$—;

T is H, $R^4$-aryl or $R^4$-heteroaryl;

Q is $R^5$-phenyl, or $R^5$-naphthyl;

$R^1$ is H, $C_{1-6}$ alkyl, —(C($R^6$)($R^7$))$_n$—G, —$G^2$, or —(C($R^6$)($R^7$))$_p$—M—(C($R^{13}$)($R^{14}$))$_n$—G;

$R^4$ and $R^5$ are independently 1–3 substituents independently selected from the group consisting of H, halogeno, —$OR^6$, —OC(O)$R^6$, —OC(O)N($R^6$)($R^7$), —N($R^6$)($R^7$), $C_{1-6}$ alkyl, —$CF_3$, —$C_2F_5$, —$COR^6$, —$CO_2R^6$, —CON($R^6$)($R^7$), —S(O)$_e$$R^{13}$, —CN, —$OCF_3$, —$OCHF_2$, —$NR^6CO_2R^{16}$, —$NR^6COR^7$, —$NR^8$CON($R^6$)($R^7$), $NO_2$, —N($R^6$)S(O)$_2$$R^{13}$ or —S(O)$_2$N($R^6$)($R^7$); or adjacent $R^4$ substituents or adjacent $R^5$ substituents can form a —O—$CH_2$—O— group;

$R^6$, $R^7$, $R^8$, $R^{13}$ and $R^{14}$ are independently selected from the group consisting of H, $C_{1-6}$ alkyl, $C_2$–$C_6$ hydroxyalkyl, $C_1$–$C_6$ alkoxy-$C_1$–$C_6$ alkyl, $R^{15}$-phenyl, and $R^{15}$-benzyl;

$R^9$ is independently selected from the group consisting of $R^6$ and —$OR^6$;

or $R^6$ and $R^7$, or $R^7$ and $R^9$, together with the nitrogen to which they are attached, form a ring of 5 to 6 members, wherein 0, 1 or 2 ring members are selected from the group consisting of —O—, —S— and —N($R^{19}$)—;

$R^{6a}$, $R^{7a}$, $R^{8a}$, $R^{9a}$, $R^{10}$ and $R^{10a}$ are independently selected from the group consisting of H and $C_{1-6}$ alkyl;

$R^{15}$ is 1 to 3 substituents independently selected from the group consisting of H, —OH, $C_1$–$C_6$ alkyl, $C_1$–$C_6$ alkoxy, $C_1$–$C_6$ alkylthio, halogeno, —$CF_3$, —$C_2F_5$, —$COR^{10}$, —$CO_2R^{10}$, —C(O)N($R^{10}$)$_2$, —S(O)$_e$$R^{10a}$, —CN, —N($R^{10}$)$COR^{10}$, —N($R^{10}$)CON($R^{10}$)$_2$ and —$NO_2$;

$R^{16}$ is $C_{1-6}$ alkyl, $R^{15}$-phenyl or $R^{15}$-benzyl;

$R^{19}$ is H, $C_1$–$C_6$ alkyl, —C(O)N($R^{10}$)$_2$ or —$CO_2R^{10}$;

n and p are independently 1–6;

G is selected from the group consisting of H, $R^4$-aryl, $R^4$-heterocycloalkyl, $R^4$-heteroaryl, $R^4$-cycloalkyl, —$CH_2F$, —$CHF_2$, —$CF_3$, —$OR^6$, —N($R^6$)($R^7$), —$COR^6$, —$CO_2R^6$, —CON($R^7$)($R^9$), —S(O)$_e$$R^{13}$, —$NR^6CO_2R^{16}$, —$NR^6COR^7$, —$NR^8$CON($R^6$)($R^7$), —N($R^6$)S(O)$_2$$R^{13}$, —N($R^6$)S(O)$_2$N($R^{33}$)($R^{34}$), —S(O)$_2$N($R^6$)($R^7$), —OC(O)$R^6$, —OC(O)N($R^6$)($R^7$), —C(=$NOR^8$)N($R^6$)($R^7$), —C(=$NR^{25}$)N($R^6$)($R^7$), —N($R^8$)C(=$NR^{25}$)N($R^6$)($R^7$), —CN, —C(O)N($R^6$)$OR^7$, and —C(O)N($R^9$)-($R^4$-heteroaryl), provided that when n is 1, G is not —OH or —N($R^6$)($R^7$);

M is selected from the group consisting of a double bond, —O—, —N($R^6$)—, —C(O)—, —C($R^6$)($OR^7$)—, —C($R^8$)(N($R^6$)($R^7$))—, —C(=$NOR^6$)N($R^7$)—, —C(N($R^6$)($R^7$))=NO—, —C(=$NR^{25}$)N($R^6$)—, —C(O)N($R^9$)—, —N($R^9$)C(O)—, —C(=S)N($R^9$)—, —N($R^9$)C(=S)— and —N($R^6$)C(O)N($R^7$)—, provided that when n is 1, G is not OH or —NH($R^6$); and when p is 2–6, M can also be —N($R^6$)C(=$NR^{25}$)N($R^7$)— or —OC(O)N($R^6$)—;

$G^2$ is $R^4$-aryl, $R^4$-heterocycloalkyl, $R^4$-heteroaryl, $R^4$-cycloalkyl, —$COR^6$, —$CO_2R^{16}$, —S(O)$_2$N($R^6$)($R^7$) or —CON($R^6$)($R^7$);

e is 0, 1 or 2, provided that when e is 1 or 2, $R^{13}$ and $R^{10a}$ are not H;

$R^{25}$ is H, $C_1$–$C_6$ alkyl, —CN, $R^{15}$-phenyl or $R^{15}$-benzyl;

Z is

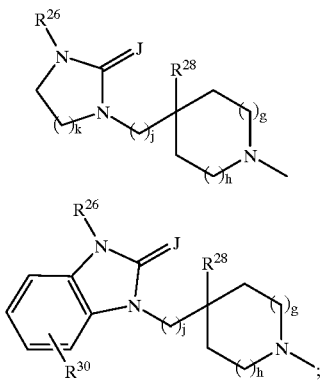

g, h and j are independently 0–2;

k is 1–4;

J is =O, =S, =$NR^9$, =NCN or =$NOR^1$;

$R^{26}$ is H, $C_{1-6}$ alkyl, —$(C(R^6)(R^7))_n$—G, —$G^2$, —C(O)—$(C(R^8)(R^9))_n$—G or —$S(O)_e R^{13}$;

$R^{28}$ is H, —$(C(R^6)(R^7))_t$—G or —$CON(R^6)(R^7)$;

t is 0, 1, 2 or 3, provided that when j is 0, t is 1, 2 or 3;

$R^{30}$ is 1–3 substituents independently selected from the group consisting of H, halogeno, —$OR^6$, —OC(O)$R^6$, —$OC(O)N(R^6)(R^7)$, —$N(R^6)(R^7)$, $C_{1-6}$ alkyl, —$CF_3$, —$C_2F_5$, —$COR^6$, —$CO_2R^6$, —$CON(R^6)(R^7)$, —$S(O)_e R^{13}$, —CN, —$OCF_3$, —$NR^6CO_2R^{16}$, —$NR^6COR^7$, —$NR^8CON(R^6)(R^7)$, $NO_2$, —$N(R^6)S(O)_2R^{13}$ or —$S(O)_2N(R^6)(R^7)$; or adjacent $R^{30}$ substituents can form a —O—$CH_2$—O— group; and $R^{33}$ and $R^{34}$ are independently selected from the group consisting of H, $C_1$–$C_6$ alkyl, $R^{15}$-phenyl and $R^{15}$-benzyl;

wherein heterocycloalkyl is a 4- to 6-membered saturated ring comprising 1 to 3 heteroatoms independently selected from the group consisting of —O—, —S— and —$N(R^{19})$—, with the remaining ring members being carbon, and heteroaryl is a 5- to 10 membered single or benzofused aromatic ring comprising 1 to 4 heteroatoms independently selected from —O—, —S— and —N=, provided that the rings do not include adjacent oxygen or sulfur atoms.

13. A compound of claim 12 wherein heterocycloalkyl is morpholinyl and heteroaryl is selected from the group consisting of pyridyl, pyridyl-N oxide, tetrazolyl, furanyl, thiazolyl and thiadiazolyl.

* * * * *

UNITED STATES PATENT AND TRADEMARK OFFICE
CERTIFICATE OF CORRECTION

PATENT NO. : 6,204,265 B1  
DATED : March 20, 2001  
INVENTOR(S) : Gregory A. Reichard, Neng-Yang Shih, Dasong Wang Page 1 of 2

It is certified that error appears in the above-identified patent and that said Letters Patent is hereby corrected as shown below:

Column 54,
Line 10, delete

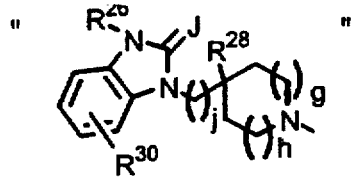

Column 55,
First line, delete

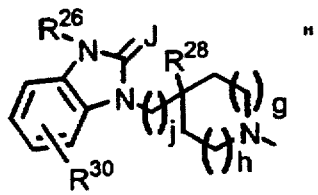

Column 55,
Line 30, delete

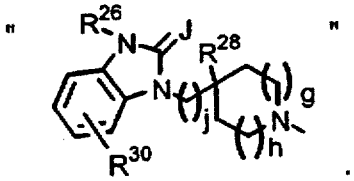

UNITED STATES PATENT AND TRADEMARK OFFICE
CERTIFICATE OF CORRECTION

PATENT NO. : 6,204,265 B1
DATED : March 20, 2001
INVENTOR(S) : Gregory A. Reichard, Neng-Yang Shih, Dasong Wang Page 2 of 2

It is certified that error appears in the above-identified patent and that said Letters Patent is hereby corrected as shown below:

Column 69,
Line 15, delete

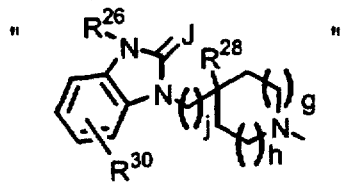

Signed and Sealed this

Fifth Day of February, 2002

Attest:

JAMES E. ROGAN
*Director of the United States Patent and Trademark Office*

*Attesting Officer*